(12) United States Patent
Hacking et al.

(10) Patent No.: US 12,402,804 B2
(45) Date of Patent: Sep. 2, 2025

(54) WEARABLE DEVICE FOR COUPLING TO A USER, AND MEASURING AND MONITORING USER ACTIVITY

(71) Applicant: ROM TECHNOLOGIES, INC., Las Vegas, NV (US)

(72) Inventors: S. Adam Hacking, Nashua, NH (US); Sucheta Tamragouri, Nashua, NH (US); Jeff Cote, Raymond, NH (US); Daniel Lipszyc, Glasgow, MT (US); Mikael Taveras, Boston, MA (US)

(73) Assignee: ROM Technologies, Inc., Brookfield, CT (US)

( * ) Notice: Subject to any disclaimer, the term of this patent is extended or adjusted under 35 U.S.C. 154(b) by 551 days.

(21) Appl. No.: 17/017,062

(22) Filed: Sep. 10, 2020

(65) Prior Publication Data

US 2021/0076981 A1 Mar. 18, 2021

Related U.S. Application Data

(60) Provisional application No. 62/991,295, filed on Mar. 18, 2020, provisional application No. 62/911,515, (Continued)

(51) Int. Cl.
- *A61B 5/107* (2006.01)
- *A61B 5/00* (2006.01)
- *A61B 5/11* (2006.01)

(52) U.S. Cl.
CPC .......... *A61B 5/1071* (2013.01); *A61B 5/1121* (2013.01); *A61B 5/6801* (2013.01); *A61B 2562/166* (2013.01)

(58) Field of Classification Search
CPC ... A61B 5/1071; A61B 5/1121; A61B 5/6801; A61B 5/4585; A61B 5/742;
(Continued)

(56) References Cited

U.S. PATENT DOCUMENTS

| 59,915 A | 11/1866 | Lallement |
| 363,522 A | 5/1887 | Knous |

(Continued)

FOREIGN PATENT DOCUMENTS

| CA | 2698078 A1 | 3/2010 |
| CA | 3193419 A1 | 3/2022 |

(Continued)

OTHER PUBLICATIONS

International Searching Authority, Search Report and Written Opinion for International Application No. PCT/US2021/038617, Date of Mailing Oct. 15, 2021, 12 pages.

(Continued)

*Primary Examiner* — Jennifer Robertson
*Assistant Examiner* — Nidhi N Patel
(74) *Attorney, Agent, or Firm* — Dickinson Wright PLLC; Jonathan H. Harder; Stephen A. Mason

(57) ABSTRACT

A system for measuring an angle of a joint of a user includes a center hub, a first arm, a second arm, a magnet, and a sensor. The center hub includes a first hub and a second hub. The first arm is configured for attachment to a first limb portion of the user at a first outer end and to the first hub at a first inner end. The second arm is configured for attachment to a second limb portion of the user at a second outer end and to the second hub at a second inner end, wherein the first hub is pivotally coupled to the second hub. The magnet is coupled to the second hub. The sensor is disposed in the center hub and configured to detect a rotation of the magnet.

5 Claims, 29 Drawing Sheets

Related U.S. Application Data filed on Oct. 7, 2019, provisional application No. 62/904,013, filed on Sep. 23, 2019, provisional application No. 62/901,464, filed on Sep. 17, 2019, provisional application No. 62/901,411, filed on Sep. 17, 2019.

(58) Field of Classification Search
CPC ... A61B 5/4528; A61B 5/6842; A61B 5/6828; A61B 5/6833; A61B 2562/166; A61B 2562/0233; A61B 2562/164; A61B 2560/0223

See application file for complete search history.

(56) References Cited

U.S. PATENT DOCUMENTS

| | | |
|---|---|---|
| 446,671 A | 2/1891 | Elliott |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorfp |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,961,570 A | 10/1990 | Chang |
| 5,161,430 A | 11/1992 | Febey |
| 5,202,794 A | 4/1993 | Schnee et al. |
| 5,247,853 A | 9/1993 | Dalebout |
| 5,282,748 A | 2/1994 | Little |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,155,958 A | 12/2000 | Goldberg |
| 6,162,189 A | 12/2000 | Girone et al. |
| 6,182,029 B1 | 1/2001 | Friedman |
| 6,253,638 B1 | 7/2001 | Bermudez |
| 6,371,891 B1 | 4/2002 | Speas |
| 6,413,190 B1 | 7/2002 | Wood et al. |
| 6,430,436 B1 | 8/2002 | Richter |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,543,309 B2 | 4/2003 | Heim |
| 6,589,139 B1 | 7/2003 | Butterworth |
| 6,601,016 B1 | 7/2003 | Brown et al. |
| 6,613,000 B1 | 9/2003 | Reinkensmeyer et al. |
| 6,626,800 B1 | 9/2003 | Casler |
| 6,640,122 B2 * | 10/2003 | Manoli ............... A61B 5/6804 607/139 |
| 6,640,662 B1 | 11/2003 | Baxter |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| 7,594,879 B2 | 9/2009 | Johnson |
| 7,628,730 B1 | 12/2009 | Watterson et al. |
| D610,635 S | 2/2010 | Hildebrandt |
| 7,815,551 B2 | 10/2010 | Merli |
| 7,969,315 B1 | 6/2011 | Ross et al. |
| 7,974,689 B2 | 7/2011 | Volpe et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,113,991 B2 | 2/2012 | Kutliroff |
| 8,177,732 B2 | 5/2012 | Einav et al. |
| 8,298,123 B2 | 10/2012 | Hickman |
| 8,371,990 B2 | 2/2013 | Shea |
| 8,515,777 B1 | 8/2013 | Rajasenan |
| 8,607,465 B1 * | 12/2013 | Edwards ............... G01B 3/56 33/471 |
| 8,751,264 B2 | 6/2014 | Beraja et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,893,287 B2 | 11/2014 | Gjonej et al. |
| 8,911,327 B1 | 12/2014 | Boyette |
| 9,004,598 B2 | 4/2015 | Weber |
| 9,311,789 B1 | 4/2016 | Gwin |
| 9,312,907 B2 | 4/2016 | Auchinleck et al. |
| 9,474,935 B2 | 10/2016 | Abbondanza et al. |
| 9,480,873 B2 | 11/2016 | Chuang |
| 9,514,277 B2 | 12/2016 | Hassing et al. |
| 9,629,558 B2 | 4/2017 | Yuen et al. |
| 9,640,057 B1 | 5/2017 | Ross |
| 9,707,147 B2 | 7/2017 | Levital et al. |
| D794,142 S | 8/2017 | Zhou |
| 9,757,612 B2 | 9/2017 | Weber |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,919,198 B2 | 3/2018 | Romeo et al. |
| 9,939,784 B1 | 4/2018 | Berardinelli |
| 9,977,587 B2 | 5/2018 | Mountain |
| 9,993,181 B2 | 6/2018 | Ross |
| 10,004,946 B2 | 6/2018 | Ross |
| D826,349 S | 8/2018 | Oblamski |
| 10,055,550 B2 | 8/2018 | Goetz |
| 10,058,473 B2 | 8/2018 | Oshima et al. |
| 10,089,443 B2 | 10/2018 | Miller et al. |
| 10,111,643 B2 | 10/2018 | Shulhauser et al. |
| 10,130,298 B2 | 11/2018 | Mokaya et al. |
| 10,137,328 B2 | 11/2018 | Baudhuin |

(56) References Cited

U.S. PATENT DOCUMENTS

| | | |
|---|---|---|
| 10,143,395 B2 | 12/2018 | Chakravarthy et al. |
| 10,173,094 B2 | 1/2019 | Gomberg et al. |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,369,021 B2 | 8/2019 | Zoss et al. |
| 10,380,866 B1 | 8/2019 | Ross et al. |
| 10,413,238 B1 | 9/2019 | Cooper |
| 10,424,033 B2 | 9/2019 | Romeo |
| D866,957 S | 11/2019 | Ross et al. |
| 10,468,131 B2 | 11/2019 | Macoviak et al. |
| 10,475,323 B2 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,569,122 B2 | 2/2020 | Johnson |
| 10,581,896 B2 | 3/2020 | Nachenberg |
| 10,646,746 B1 | 5/2020 | Gomberg et al. |
| 10,786,181 B1 * | 9/2020 | Echols ................ A61B 5/1122 |
| D899,605 S | 10/2020 | Ross et al. |
| 10,867,695 B2 | 12/2020 | Neagle |
| D907,143 S | 1/2021 | Ach et al. |
| 10,881,911 B2 | 1/2021 | Kwon et al. |
| 10,987,176 B2 | 4/2021 | Poltaretskyi et al. |
| 10,991,463 B2 | 4/2021 | Kutzko et al. |
| 11,065,170 B2 | 7/2021 | Yang et al. |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,278,766 B2 | 3/2022 | Lee |
| 11,298,284 B2 | 4/2022 | Bayerlein |
| 11,325,005 B2 | 5/2022 | Mason et al. |
| 11,376,470 B2 | 7/2022 | Weldemariam |
| 11,422,841 B2 | 8/2022 | Jeong |
| 11,495,355 B2 | 11/2022 | McNutt et al. |
| 11,508,258 B2 | 11/2022 | Nakashima et al. |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,636,944 B2 | 4/2023 | Hanrahan et al. |
| 11,663,673 B2 | 5/2023 | Pyles |
| 11,701,548 B2 | 7/2023 | Posnack et al. |
| 11,957,960 B2 | 4/2024 | Bissonnette et al. |
| 2001/0044573 A1 | 11/2001 | Manoli |
| 2002/0143279 A1 * | 10/2002 | Porier ................ A61B 5/1071 602/5 |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0083596 A1 * | 5/2003 | Kramer ................ A61B 5/1071 600/595 |
| 2003/0092536 A1 | 5/2003 | Romanelli et al. |
| 2003/0109814 A1 | 6/2003 | Rummerfield |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0204959 A1 | 10/2004 | Moreano et al. |
| 2005/0020411 A1 | 1/2005 | Andrews |
| 2005/0085346 A1 | 4/2005 | Johnson |
| 2005/0085353 A1 | 4/2005 | Johnson |
| 2005/0115561 A1 | 6/2005 | Stahmann |
| 2005/0274220 A1 | 12/2005 | Reboullet |
| 2006/0003871 A1 | 1/2006 | Houghton |
| 2006/0058648 A1 | 3/2006 | Meier |
| 2006/0064136 A1 | 3/2006 | Wang |
| 2006/0064329 A1 | 3/2006 | Abolfathi et al. |
| 2006/0247095 A1 | 11/2006 | Rummerfield |
| 2007/0118389 A1 | 5/2007 | Shipon |
| 2007/0184414 A1 | 8/2007 | Perez |
| 2007/0194939 A1 | 8/2007 | Alvarez et al. |
| 2007/0219059 A1 | 9/2007 | Schwartz |
| 2008/0082356 A1 | 4/2008 | Friedlander et al. |
| 2008/0161166 A1 | 7/2008 | Lo |
| 2008/0161733 A1 | 7/2008 | Einav et al. |
| 2008/0221485 A1 * | 9/2008 | Lissek ................ A61B 5/1071 600/595 |
| 2008/0281633 A1 | 11/2008 | Burdea et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mul'e |
| 2009/0287503 A1 | 11/2009 | Angell et al. |
| 2009/0299766 A1 | 12/2009 | Friedlander et al. |
| 2010/0076786 A1 | 3/2010 | Dalton et al. |
| 2010/0121160 A1 | 5/2010 | Stark et al. |
| 2010/0216168 A1 | 8/2010 | Heinzman et al. |
| 2010/0248905 A1 | 9/2010 | Lu |
| 2010/0268304 A1 | 10/2010 | Matos |
| 2010/0326207 A1 | 12/2010 | Topel |
| 2011/0010188 A1 | 1/2011 | Yoshikawa et al. |
| 2011/0119212 A1 | 5/2011 | De Bruin et al. |
| 2011/0172059 A1 | 7/2011 | Watterson et al. |
| 2011/0218814 A1 | 9/2011 | Coats |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0167709 A1 | 7/2012 | Chen et al. |
| 2012/0190502 A1 | 7/2012 | Paulus et al. |
| 2012/0259648 A1 | 10/2012 | Mallon et al. |
| 2012/0296455 A1 | 11/2012 | Ohnemus et al. |
| 2012/0310667 A1 | 12/2012 | Altman et al. |
| 2013/0123667 A1 | 5/2013 | Komatireddy et al. |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0332616 A1 | 12/2013 | Landwehr |
| 2014/0006042 A1 | 1/2014 | Keefe et al. |
| 2014/0089836 A1 | 3/2014 | Damani et al. |
| 2014/0113261 A1 | 4/2014 | Akiba |
| 2014/0172442 A1 | 6/2014 | Broderick |
| 2014/0188009 A1 | 7/2014 | Lange et al. |
| 2014/0194250 A1 | 7/2014 | Reich et al. |
| 2014/0228649 A1 | 8/2014 | Rayner et al. |
| 2014/0246499 A1 | 9/2014 | Proud et al. |
| 2014/0257837 A1 | 9/2014 | Walker et al. |
| 2014/0303540 A1 | 10/2014 | Baym |
| 2014/0315689 A1 | 10/2014 | Vauquelin et al. |
| 2014/0322686 A1 | 10/2014 | Kang |
| 2014/0371816 A1 | 12/2014 | Matos |
| 2015/0025816 A1 | 1/2015 | Ross |
| 2015/0073814 A1 | 3/2015 | Linebaugh |
| 2015/0088544 A1 | 3/2015 | Goldberg |
| 2015/0099458 A1 | 4/2015 | Weisner et al. |
| 2015/0099952 A1 | 4/2015 | Lain et al. |
| 2015/0112230 A1 | 4/2015 | Iglesias |
| 2015/0130830 A1 | 5/2015 | Nagasaki |
| 2015/0141200 A1 | 5/2015 | Murray et al. |
| 2015/0149217 A1 | 5/2015 | Kaburagi |
| 2015/0161331 A1 | 6/2015 | Oleynik |
| 2015/0196805 A1 | 7/2015 | Koduri |
| 2015/0257679 A1 | 9/2015 | Ross |
| 2015/0265209 A1 | 9/2015 | Zhang |
| 2015/0339442 A1 | 11/2015 | Oleynik |
| 2015/0351664 A1 | 12/2015 | Ross |
| 2015/0351665 A1 | 12/2015 | Ross |

(56) References Cited

U.S. PATENT DOCUMENTS

| | | |
|---|---|---|
| 2015/0379430 A1 | 12/2015 | Dirac et al. |
| 2016/0023081 A1 | 1/2016 | Popa-Simil |
| 2016/0045170 A1 | 2/2016 | Migita |
| 2016/0096073 A1 | 4/2016 | Rahman et al. |
| 2016/0140319 A1 | 5/2016 | Stark |
| 2016/0143593 A1 | 5/2016 | Fu et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0302721 A1 | 10/2016 | Wiedenhoefer et al. |
| 2016/0322078 A1 | 11/2016 | Bose et al. |
| 2016/0354636 A1 | 12/2016 | Jang |
| 2016/0373477 A1 | 12/2016 | Moyle |
| 2017/0004260 A1 | 1/2017 | Moturu et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0113092 A1 | 4/2017 | Johnson |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0181698 A1 | 6/2017 | Wiedenhoefer et al. |
| 2017/0202724 A1 | 7/2017 | De Rossi |
| 2017/0220751 A1 | 8/2017 | Davis |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0262604 A1 | 9/2017 | Francois |
| 2017/0265800 A1 | 9/2017 | Auchinleck et al. |
| 2017/0270260 A1 | 9/2017 | Shetty |
| 2017/0278209 A1 | 9/2017 | Olsen et al. |
| 2017/0281390 A1* | 10/2017 | Abdul-Hafiz ........... A61F 5/013 |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2018/0052962 A1 | 2/2018 | Van Der Koijk et al. |
| 2018/0056104 A1 | 3/2018 | Cromie et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0078843 A1 | 3/2018 | Tran et al. |
| 2018/0102190 A1 | 4/2018 | Hogue et al. |
| 2018/0116741 A1* | 5/2018 | Garcia Kilroy ....... G01L 3/1428 |
| 2018/0140927 A1 | 5/2018 | Kito |
| 2018/0146870 A1 | 5/2018 | Shemesh |
| 2018/0177612 A1 | 6/2018 | Trabish et al. |
| 2018/0220935 A1 | 8/2018 | Tadano et al. |
| 2018/0240552 A1 | 8/2018 | Tuyl et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0271432 A1 | 9/2018 | Auchinleck et al. |
| 2018/0280784 A1 | 10/2018 | Romeo et al. |
| 2018/0290017 A1 | 10/2018 | Fung |
| 2018/0296143 A1 | 10/2018 | Anderson et al. |
| 2018/0318122 A1 | 11/2018 | LeCursi et al. |
| 2018/0330810 A1 | 11/2018 | Gamarnik |
| 2018/0330824 A1 | 11/2018 | Athey et al. |
| 2018/0353812 A1 | 12/2018 | Lannon et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0080802 A1 | 3/2019 | Ziobro et al. |
| 2019/0090744 A1 | 3/2019 | Mahfouz |
| 2019/0117128 A1* | 4/2019 | Chen .................... A61B 5/1121 |
| 2019/0118038 A1 | 4/2019 | Tana et al. |
| 2019/0126099 A1 | 5/2019 | Hoang |
| 2019/0134454 A1 | 5/2019 | Mahoney et al. |
| 2019/0167988 A1 | 6/2019 | Shahriari et al. |
| 2019/0200920 A1 | 7/2019 | Tien et al. |
| 2019/0209891 A1 | 7/2019 | Fung |
| 2019/0223797 A1 | 7/2019 | Tran |
| 2019/0228856 A1 | 7/2019 | Leifer |
| 2019/0244540 A1 | 8/2019 | Errante et al. |
| 2019/0251456 A1 | 8/2019 | Constantin |
| 2019/0262084 A1 | 8/2019 | Roh |
| 2019/0269343 A1 | 9/2019 | Ramos Murguialday et al. |
| 2019/0314681 A1 | 10/2019 | Yang |
| 2019/0344123 A1 | 11/2019 | Rubin et al. |
| 2019/0362242 A1 | 11/2019 | Pillai et al. |
| 2020/0034665 A1 | 1/2020 | Ghanta |
| 2020/0038703 A1 | 2/2020 | Cleary et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0237291 A1 | 7/2020 | Raja |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0365256 A1 | 11/2020 | Hayashitani et al. |
| 2020/0401224 A1 | 12/2020 | Cotton |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0077860 A1 | 3/2021 | Posnack et al. |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0134412 A1 | 5/2021 | Guaneri et al. |
| 2021/0134425 A1 | 5/2021 | Mason et al. |
| 2021/0134428 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0244998 A1 | 8/2021 | Hacking et al. |
| 2021/0251562 A1 | 8/2021 | Jain |
| 2021/0272677 A1 | 9/2021 | Barbee |

(56) References Cited

U.S. PATENT DOCUMENTS

| | | |
|---|---|---|
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack |
| 2022/0016480 A1 | 1/2022 | Bissonnette et al. |
| 2022/0016482 A1 | 1/2022 | Bissonnette |
| 2022/0016485 A1 | 1/2022 | Bissonnette et al. |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette |
| 2022/0080265 A1 | 3/2022 | Watterson |
| 2022/0105390 A1 | 4/2022 | Yuasa |
| 2022/0118218 A1 | 4/2022 | Bense et al. |
| 2022/0133576 A1 | 5/2022 | Choi et al. |
| 2022/0176039 A1 | 6/2022 | Intereur et al. |
| 2022/0181004 A1 | 6/2022 | Zilca et al. |
| 2022/0193491 A1 | 6/2022 | Mason |
| 2022/0238223 A1 | 7/2022 | Mason |
| 2022/0262504 A1 | 8/2022 | Bratty et al. |
| 2022/0273985 A1 | 9/2022 | Jeong et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0330823 A1 | 10/2022 | Janssen |
| 2022/0338761 A1 | 10/2022 | Maddahi et al. |
| 2022/0339052 A1 | 10/2022 | Kim |
| 2022/0395232 A1 | 12/2022 | Locke |
| 2022/0401783 A1 | 12/2022 | Choi |
| 2023/0001268 A1 | 1/2023 | Bissonnette et al. |
| 2023/0029639 A1 | 2/2023 | Roy |
| 2023/0119461 A1 | 4/2023 | Mason |
| 2023/0190100 A1 | 6/2023 | Stump |
| 2023/0197240 A1 | 6/2023 | Rosenberg |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |
| 2024/0203580 A1 | 6/2024 | Mason |

FOREIGN PATENT DOCUMENTS

| | | |
|---|---|---|
| CN | 2885238 Y | 4/2007 |
| CN | 101964151 A | 2/2011 |
| CN | 201889024 U | 7/2011 |
| CN | 102670381 A | 9/2012 |
| CN | 103263336 A | 8/2013 |
| CN | 103390357 A | 11/2013 |
| CN | 103473631 A | 12/2013 |
| CN | 103501328 A | 1/2014 |
| CN | 103721343 A | 4/2014 |
| CN | 203677851 U | 7/2014 |
| CN | 103136447 B | 8/2016 |
| CN | 205626871 U | 10/2016 |
| CN | 106236502 A | 12/2016 |
| CN | 106621195 A | 5/2017 |
| CN | 107551475 A | 1/2018 |
| CN | 107930021 A | 4/2018 |
| CN | 207220817 U | 4/2018 |
| CN | 208224811 A | 12/2018 |
| CN | 109191954 A | 1/2019 |
| CN | 109363887 A | 2/2019 |
| CN | 110201358 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111111110 A | 5/2020 |
| CN | 111460305 A | 7/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 4330269 A1 | 3/1995 |
| EP | 1159989 A1 | 12/2001 |
| EP | 1968028 | 9/2008 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 3127393 A1 | 3/2023 |
| GB | 2591542 B | 3/2022 |
| IN | 201811043670 A | 7/2018 |
| JP | 2000005339 A | 1/2000 |
| JP | 2005227928 A | 8/2005 |
| JP | 2005227928 A1 | 8/2005 |
| JP | 2009011517 A | 1/2009 |
| JP | 2009112336 A | 5/2009 |
| JP | 3193662 U | 10/2014 |

(56) References Cited

FOREIGN PATENT DOCUMENTS

| | | |
|---|---|---|
| JP | 5804063 B2 | 11/2015 |
| JP | 2018102842 A | 7/2018 |
| JP | 2019028647 A | 2/2019 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 200276919 Y1 | 5/2002 |
| KR | 100582596 B1 | 5/2006 |
| KR | 101042258 B1 | 6/2011 |
| KR | 20110099953 A | 9/2011 |
| KR | 101258250 B1 | 4/2013 |
| KR | 101325581 B1 | 11/2013 |
| KR | 20140128630 A | 11/2014 |
| KR | 20150078191 A | 7/2015 |
| KR | 101580071 B1 | 12/2015 |
| KR | 101647620 B1 | 8/2016 |
| KR | 20180004928 A | 1/2018 |
| KR | 20190029175 A | 3/2019 |
| KR | 101988167 B1 | 6/2019 |
| KR | 101969392 B1 | 8/2019 |
| KR | 102055279 B1 | 12/2019 |
| KR | 102088333 B1 | 3/2020 |
| KR | 20200029180 A | 3/2020 |
| KR | 102097190 B1 | 4/2020 |
| KR | 102121586 B1 | 6/2020 |
| KR | 20200119665 A | 10/2020 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 A | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | M638437 U | 3/2023 |
| WO | 2001056465 A1 | 8/2001 |
| WO | 02093312 A2 | 11/2002 |
| WO | 2005018453 A1 | 3/2005 |
| WO | 2007102709 A1 | 9/2007 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2015026744 A1 | 2/2015 |
| WO | 2015065298 A1 | 5/2015 |
| WO | 2015082555 A1 | 6/2015 |
| WO | 2017030781 A1 | 2/2017 |
| WO | 2017091691 A1 | 6/2017 |
| WO | 2017165238 A1 | 9/2017 |
| WO | 2018081795 A1 | 5/2018 |
| WO | 2019204876 A1 | 4/2019 |
| WO | 2019143940 A1 | 7/2019 |
| WO | 2020185769 A1 | 3/2020 |
| WO | 2020256577 A1 | 12/2020 |
| WO | 2021055427 A1 | 3/2021 |
| WO | 2021055491 A1 | 3/2021 |
| WO | 2021081094 A1 | 4/2021 |
| WO | 2021090267 A1 | 5/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024107807 A1 | 5/2024 |

OTHER PUBLICATIONS

Claris Healthcare Inc.; Claris Reflex Patient Rehabilitation System Brochure, https://clarisreflex.com/, retrieved from internet on Oct. 2, 2019; 5 pages.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform For Personalized Predictive Analytics", ProQuest LLC, Jul. 2017, 185 pages.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

(56) References Cited

OTHER PUBLICATIONS

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Gerbild et al., "Physical Activity to Improve Erectile Dysfunction: A Systematic Review of Intervention Studies," Sexual Medicine, 2018, 15 pages.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.

\* cited by examiner

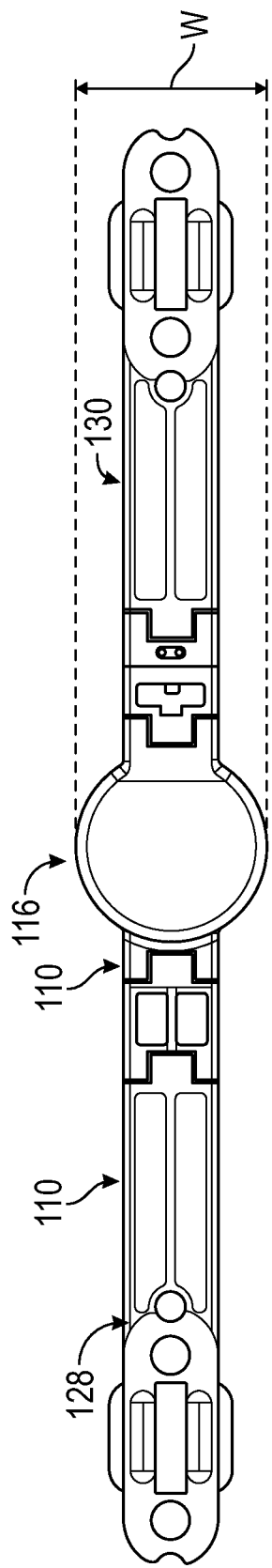
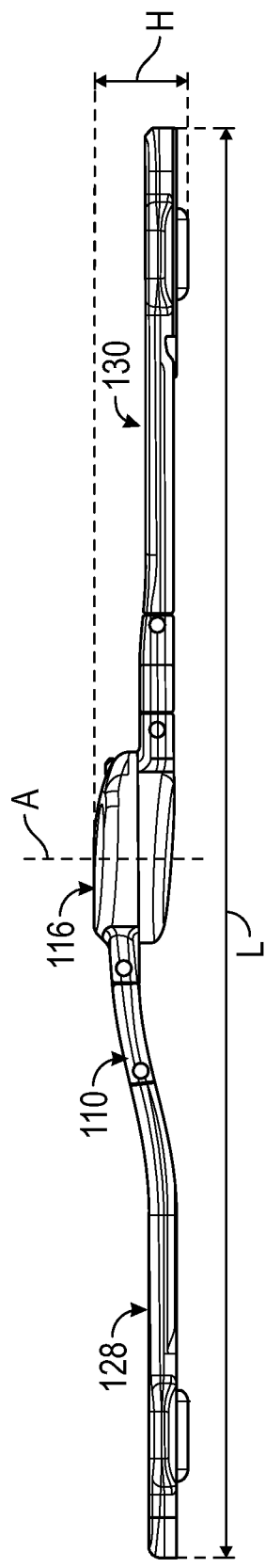
FIG. 3A
FIG. 3B

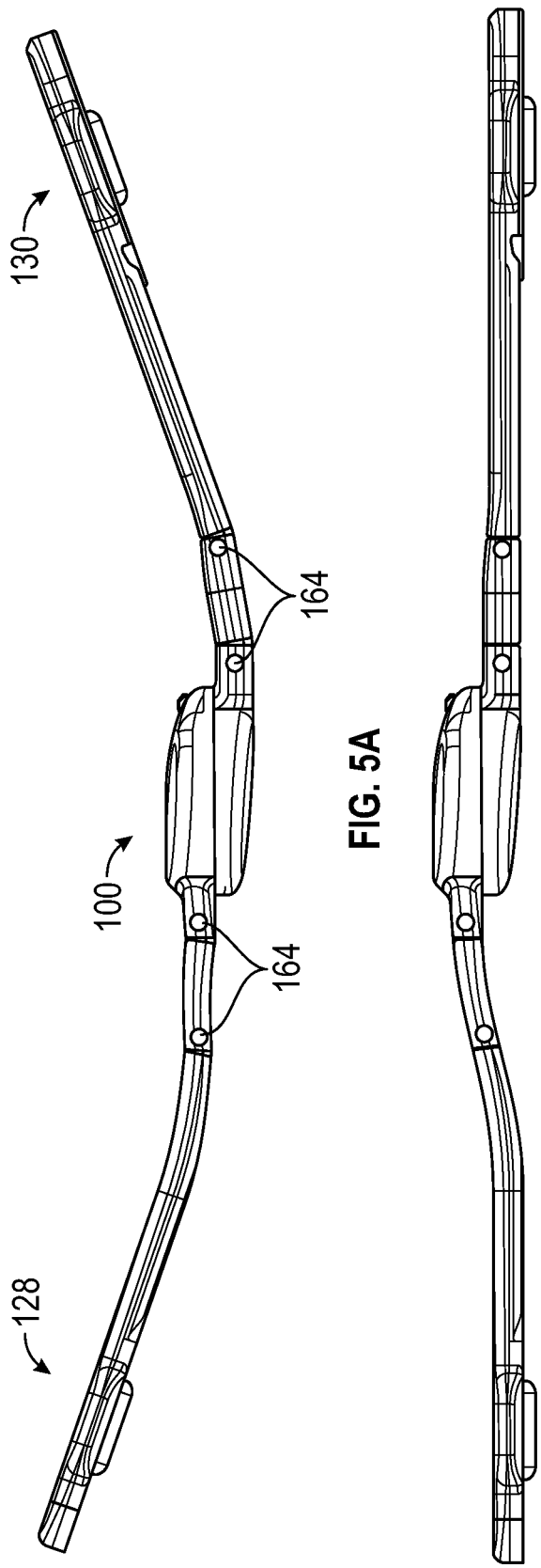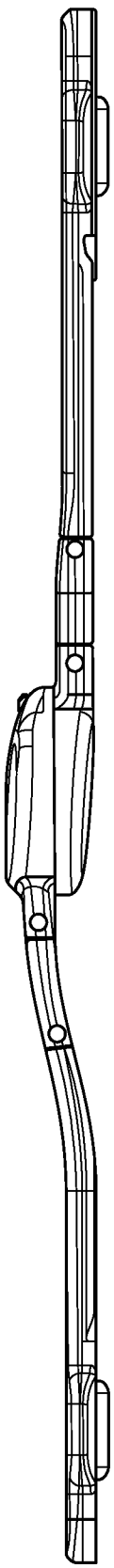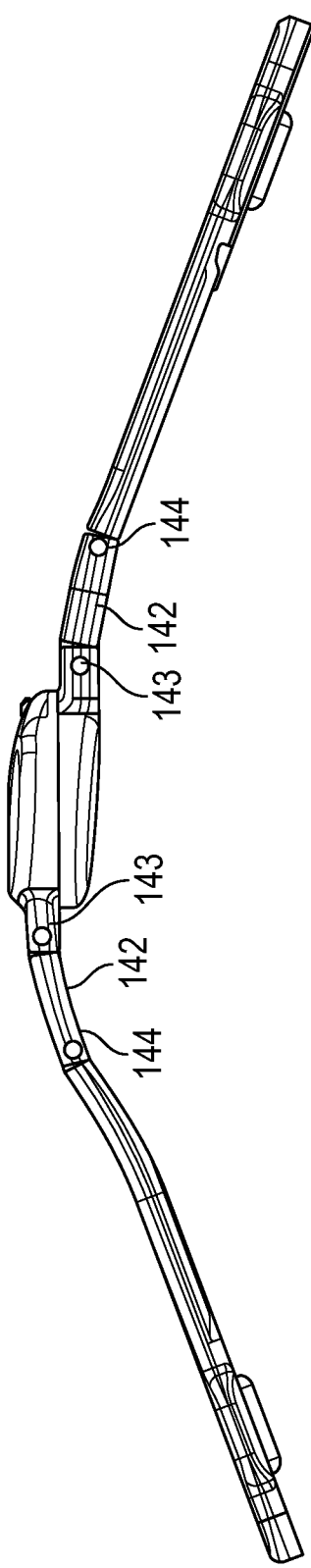

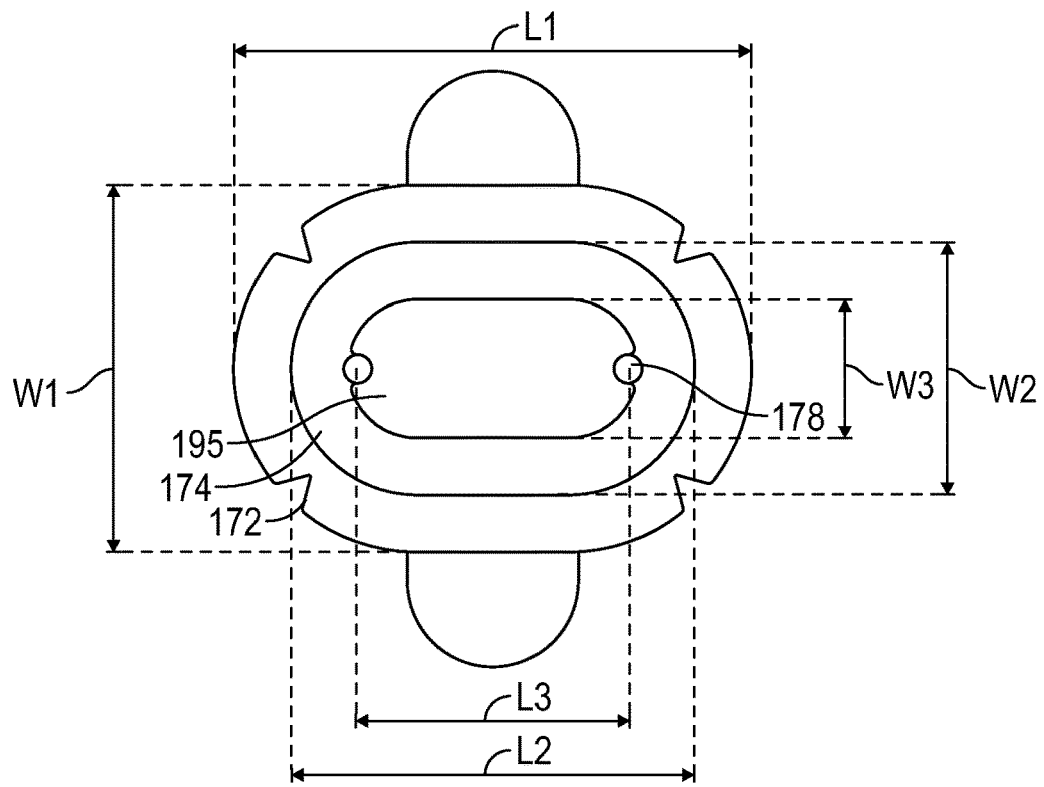
FIG. 9A
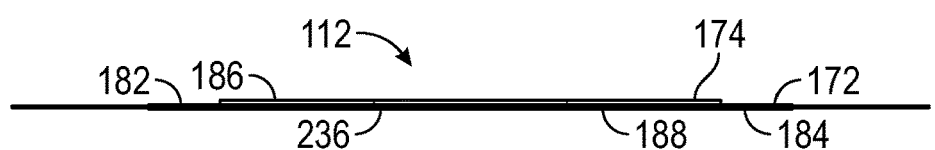
FIG. 9B
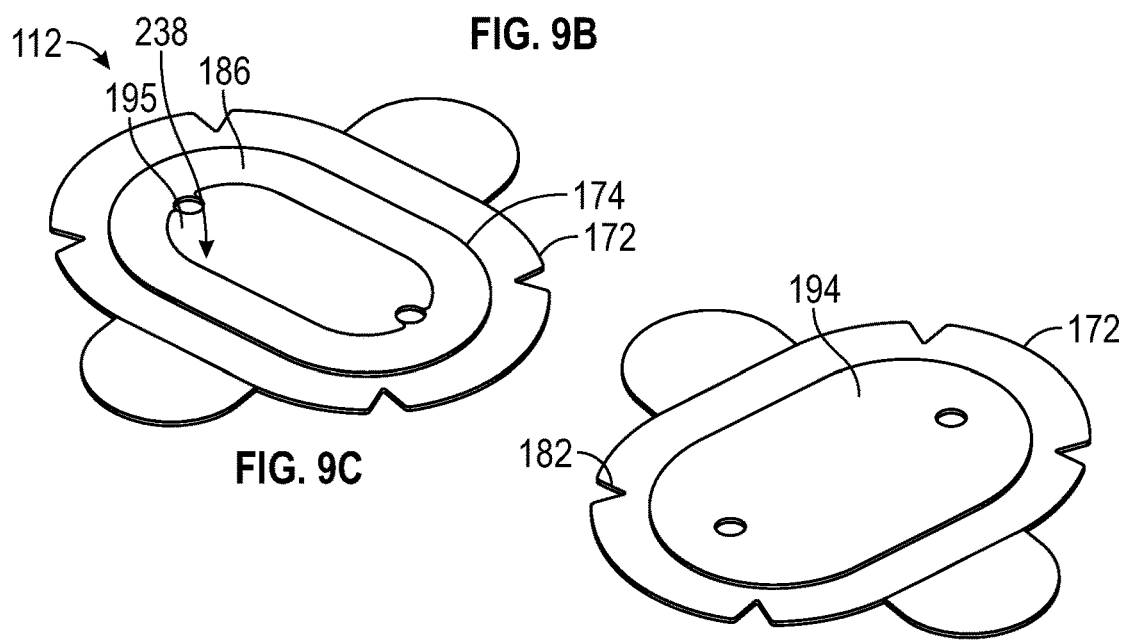
FIG. 9C
FIG. 9D

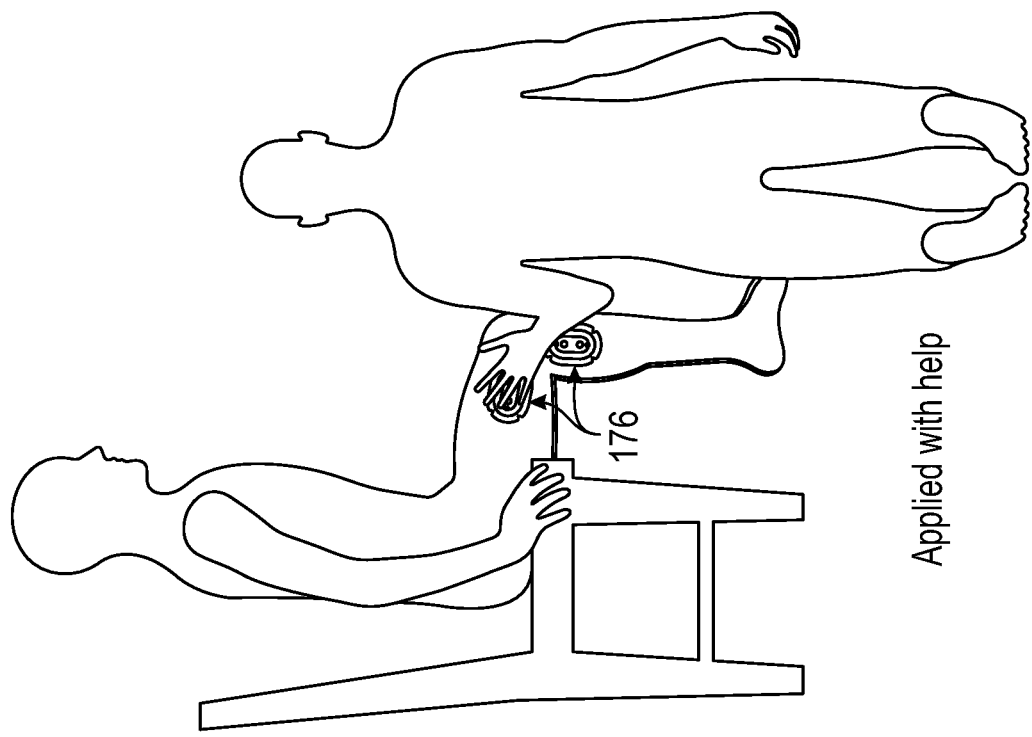
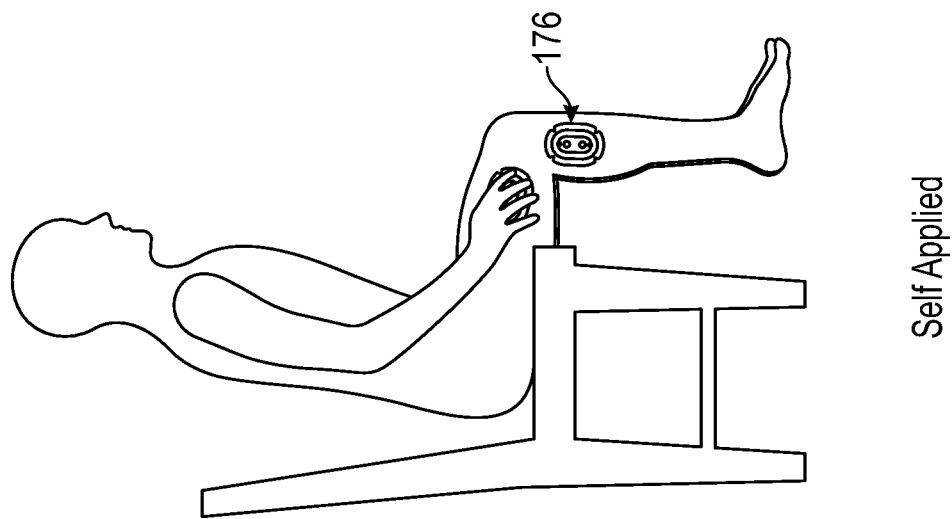
FIG. 25

WEARABLE DEVICE FOR COUPLING TO A USER, AND MEASURING AND MONITORING USER ACTIVITY

CROSS-REFERENCE TO RELATED APPLICATIONS

This application claims priority to and the benefit of: U.S. Prov. Pat. App. No. 62/991,295, filed Mar. 18, 2020, U.S. Prov. Pat. App. No. 62/911,515, filed Oct. 7, 2019, U.S. Prov. Pat. App. No. 62/904,013, filed Sep. 23, 2019, U.S. Prov. Pat. App. No. 62/901,464, filed Sep. 17, 2019, and U.S. Prov. Pat. App. No. 62/901,411, filed Sep. 17, 2019, each of which is incorporated herein by reference in its entirety.

TECHNICAL FIELD

This disclosure generally relates to wearable devices and, in particular, to coupling a wearable device to a user and measuring and monitoring activity of the user.

BACKGROUND

A patient often requires physical therapy to recover from surgery, such as a knee replacement surgery. The physical therapy can include exercise to increase the patient's strength, flexibility and stability. If a patient over-extends his or her muscles or joints, the muscles or joints, surrounding tissues or repaired tissues may become further injured. If a patient does not exercise his or her muscles or joints to gain the appropriate range of motion, the joint may become stiff and require additional surgery. Measuring and monitoring the range of motion during physical therapy can help prevent further injury to the patient and result in a faster recovery time.

A goniometer is an instrument that can be used to measure ranges of motion or joint angles of a patient's body. A standard goniometer consists of a stationary arm that cannot move independently, a moving arm attached to a fulcrum in the center of a body, and the body being a protractor of which 0 to 180 or 360 degrees are drawn. The stationary arm is attached to one limb or part of the patient's body (e.g., a thigh) and the moving arm is attached to another limb or part of the patient's body (e.g., a lower leg). The fulcrum can be a rivet or screw-like device at the center of the body that allows the moving arm to move freely on the body of the device in order for a clinician to obtain a measurement of the angle of movement of the patient's joint (e.g., a knee). The measurements can be used to track progress in a rehabilitation program. Each time a patient has a rehabilitation session, the clinician places and hold, or attaches the goniometer device onto the patient, for example, using straps. The patient may have different clinicians setting up the goniometer device and measuring the joint movement. Based on the experience of the clinician, or other person, the goniometer device may be attached onto different locations on the patient, which can affect the accuracy and reproducibility of the measurements. The accuracy of the repeated measurements may also be compromised due to issues with or the sensitivity of the device.

SUMMARY

Exemplary implementations of a system for measuring an angle of a joint of a user are disclosed. The system can include a center hub, a first arm, a second arm, a magnet, and a sensor. The center hub includes a first hub and a second hub. The first arm is configured for attachments to a first limb portion of the user at a first outer end and to the first hub at a first inner end. The second arm is configured for attachments to a second limb portion of the user at a second outer end and to the second hub at a second inner end, wherein the first hub is pivotally coupled to the second hub. The magnet is coupled to the second hub. The sensor is disposed in the center hub and configured to detect a rotation of the magnet.

Other implementations of a system for measuring an angle of a joint of a user can include a center hub, first and second coupling apparatuses, and first and second arms. The center hub has a first hub and a second hub. The first arm is configured for attachment to a first limb portion of the user at a first outer end and to the first hub at a first inner end. The second arm is configured for attachment to a second limb portion of the user at a second outer end and to the second hub at a second inner end, wherein the first hub is pivotally coupled to the second hub and configured to rotate 360 degrees about an axis. The system further comprises a magnet, a printed circuit board (PCB), and a sensor. The magnet is coupled to the second hub. The PCB is removably disposed in the center hub. The sensor is coupled to the PCB and configured to detect a rotation of the magnet.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

For a detailed description of example embodiments, reference will now be made to the accompanying drawings in which:

FIGS. 3A and 3B are top and side views of a goniometer in accordance with aspects of the present disclosure.

FIGS. 5A-C are side views of the goniometer with its arms rotating in accordance with aspects of the present disclosure.

FIGS. 9A-D are views of first and second layers of the attachment in accordance with aspects of the present disclosure.

FIGS. 25-34 are schematic sequential images of an embodiment of alignment and installation method.

NOTATION AND NOMENCLATURE

Figure 1A:
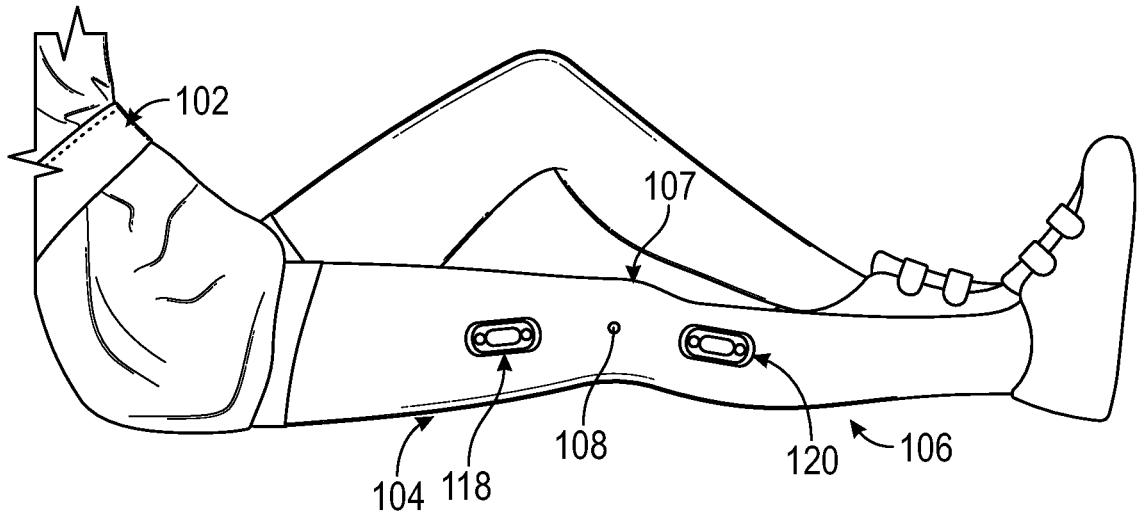
FIGS. 1A and 1B are perspective views of a wearable device for measuring and recording movement in accordance with aspects of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1B:
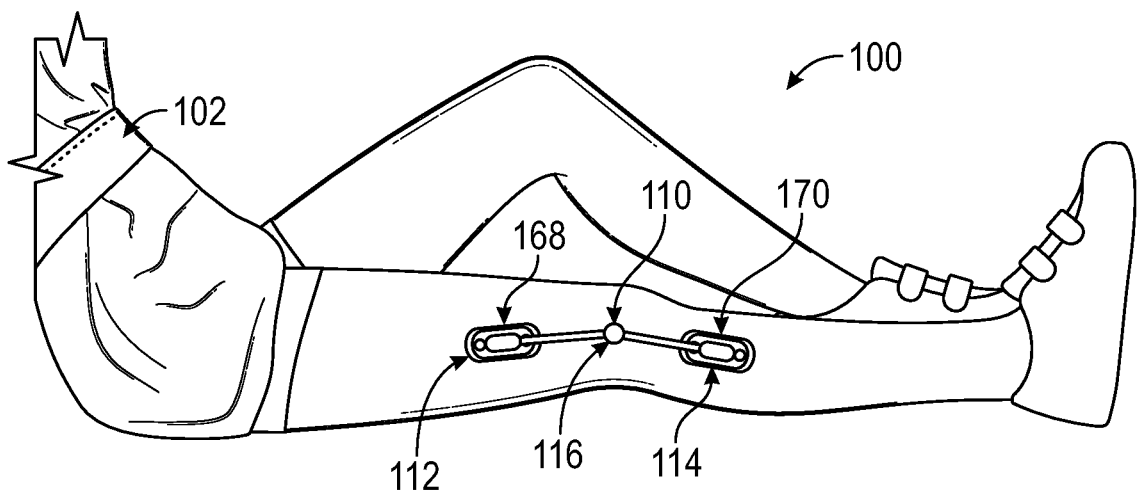
Figure 2A:
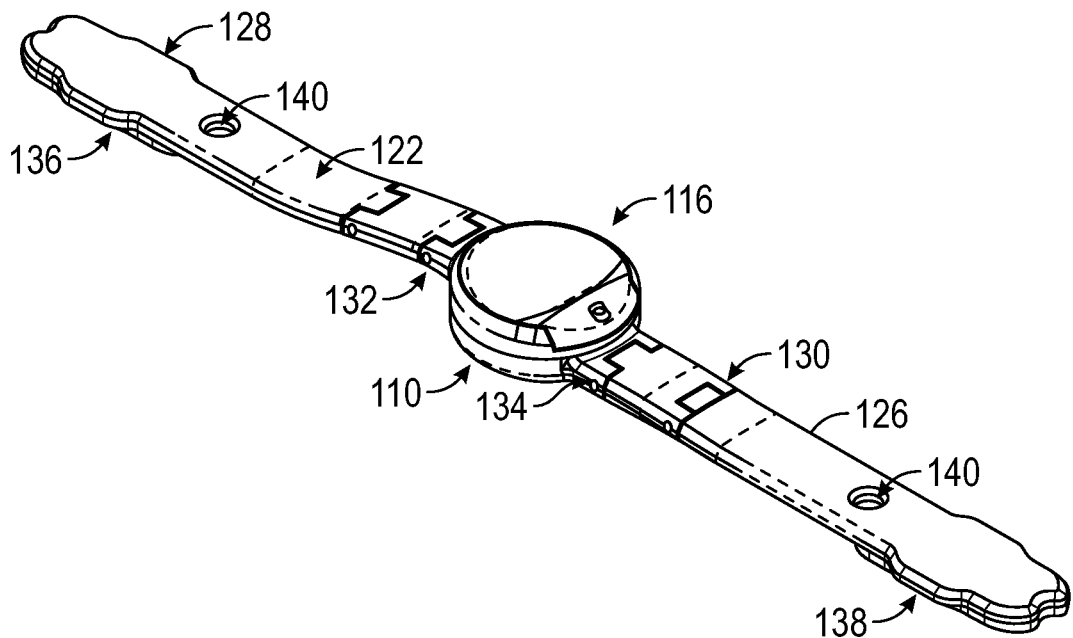
FIGS. 2A and 2B are top and bottom perspective views of a goniometer in accordance with aspects of the present disclosure.
Figure 2B:
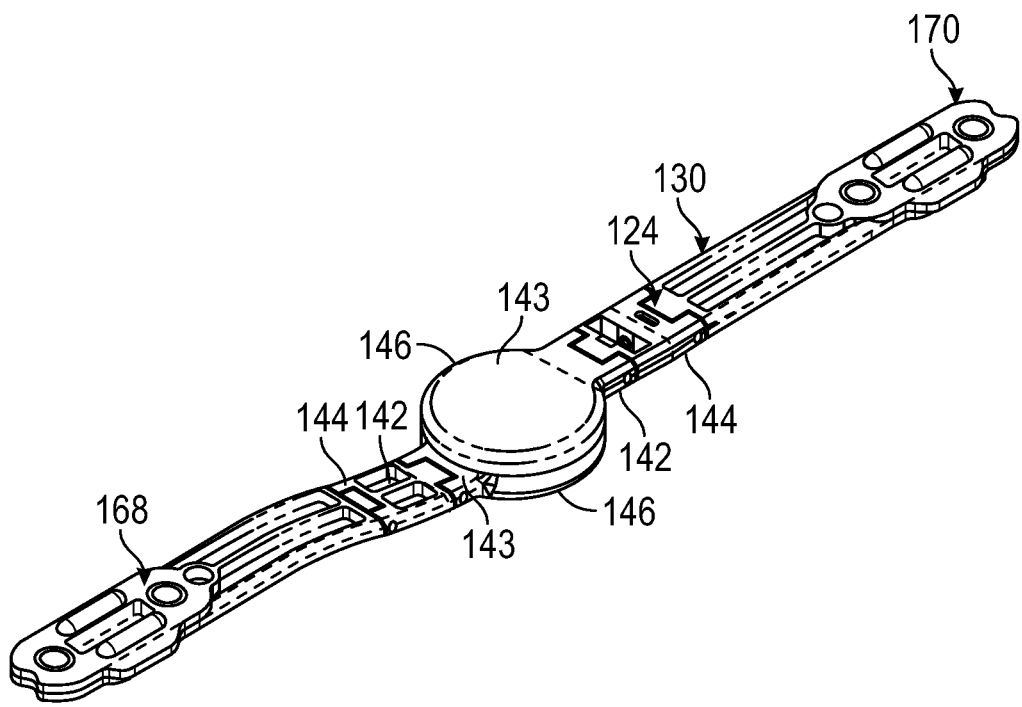

In accordance with aspects of the present disclosure, FIGS. 1A and 1B illustrate an exemplary system or wearable device 100 for measuring and recording flexion and extension at a joint 107 of a user 102. The wearable device 100 comprises first and second coupling apparatuses, or attachments, 112, 114, 118, 120 (hereinafter referred to as first and second attachments 118, 120) and may be configured to be removably coupled to the user 102 at opposing limb portions 104, 106 of the joint 107. For example, and as illustrated in FIGS. 1A and 1B, the first and second attachments 118, 120 may be coupled to a leg of a user at opposing limb portions 104, 106, e.g., thigh 104, and calf 106, of the knee or joint 107 of the user 102. As will be appreciated by those of skill in the art, the first and second attachments 118, 120 may be coupled to the user at opposing limb portions of any other joint of a patient or user 102. It is further contemplated that the wearable device 100 may be utilized for measuring flexion and extension of joints in animals, a joint of a robot, or any other desired joint or joint equivalent.

To position the wearable device 100 relative to the joint 107, a person, such as a clinician, may identify a joint center 108, where the joint center 108 may be used to align the wearable device 100 to the joint 107. The clinician may use an alignment device 300 to identify and mark the joint center 108. For example, the alignment device 300 may be used to mark the skin of the user 102 at the joint center 108 with a marker, pen, or any other desired tool. Further, the alignment device 300 may be used to identify and mark positions at opposing limb portions 104, 106 for the first and second attachments 118, 120 relative to the joint center.

With reference to FIGS. 2A-6, the wearable device 100 comprises an exemplary device or apparatus 110, such as a goniometer. Hereinafter, the device or apparatus 110 may be referred to as a goniometer 110. The goniometer 110 is configured to measure the angular flexion and extension at the joint 107 of the user 102. The goniometer 110 has a top 122, a bottom 124, and opposing sides 126. The goniometer 110 may comprise a center hub 116 aligned coaxially with an axis A, and first and second arms 128, 130, wherein the arms 128, 130 couple to, and are rotatable about, the axis A and the center hub 116. More specifically, first and second inner ends 132, 134 of the respective arms 128, 130 couple to the center hub 116. The arms 128, 130 extend outwardly from the center hub 116 to respective first and second outer ends 168, 170. In an alternative embodiment, the arms 128, 130 may be integrally formed with the center hub 116. Embodiments of the goniometer can enable various rotational or pivotal motions, such as with an axle, a rack and pinion system, etc.

With reference to FIGS. 3A and 3B, the goniometer 110 can have a length L that extends from the first outer end 136 to the second outer end 138. The length L can vary depending on the relative position of the first and second arms 128, 130. For example, a maximum length L of the goniometer 110 may be measured when the arms 128, 130 are positioned opposing one another. Whereas, when the arms 128, 130 are positioned parallel, and respectively directly above and below one another, a minimum length L of the goniometer 110 may be measured between the outer ends 136, 138 to an opposite side of the center hub 116. A width W of the goniometer may be measured as a diameter of the center hub 116. Further, a height H of the goniometer 110 may be measured from a bottom of the second arm 130 to a top of the first arm 128, or to a top of the center hub 116, whichever is greater.

In an exemplary embodiment, the center hub 116 comprises a first or upper hub 146 and a second or lower hub 148. The hubs 146, 148 are coaxially aligned with one another, and with axis A. Moreover, the hubs 146, 148 may be configured to rotate about the axis A for 360 degrees, and relative to one another. Further, each of the hubs 146, 148 may have a link arm 143 for coupling between the hubs 146, 148 and the respective arms 128, 130. For example, the first arm 128 may be coupled to the link arm 143 of the first hub 146, and the second arm 130 may be coupled to the link arm 143 of the second hub 148.

In operation, embodiments of the arms 128, 130 may rotate, pivot, flex or extend relative to the center hub 116. This design can account for the complex motion of a joint, slippage of the joint, and the broad range of shapes and sizes of the patient's joint 107. In addition, this design can maintain the position of the center hub relative to the joint center 108. Embodiments of the device can enable freedom of motion in many planes but not in the rotational plane of the joint. This enables the device to fit many different people but still make accurate measurements.

Figure 4:
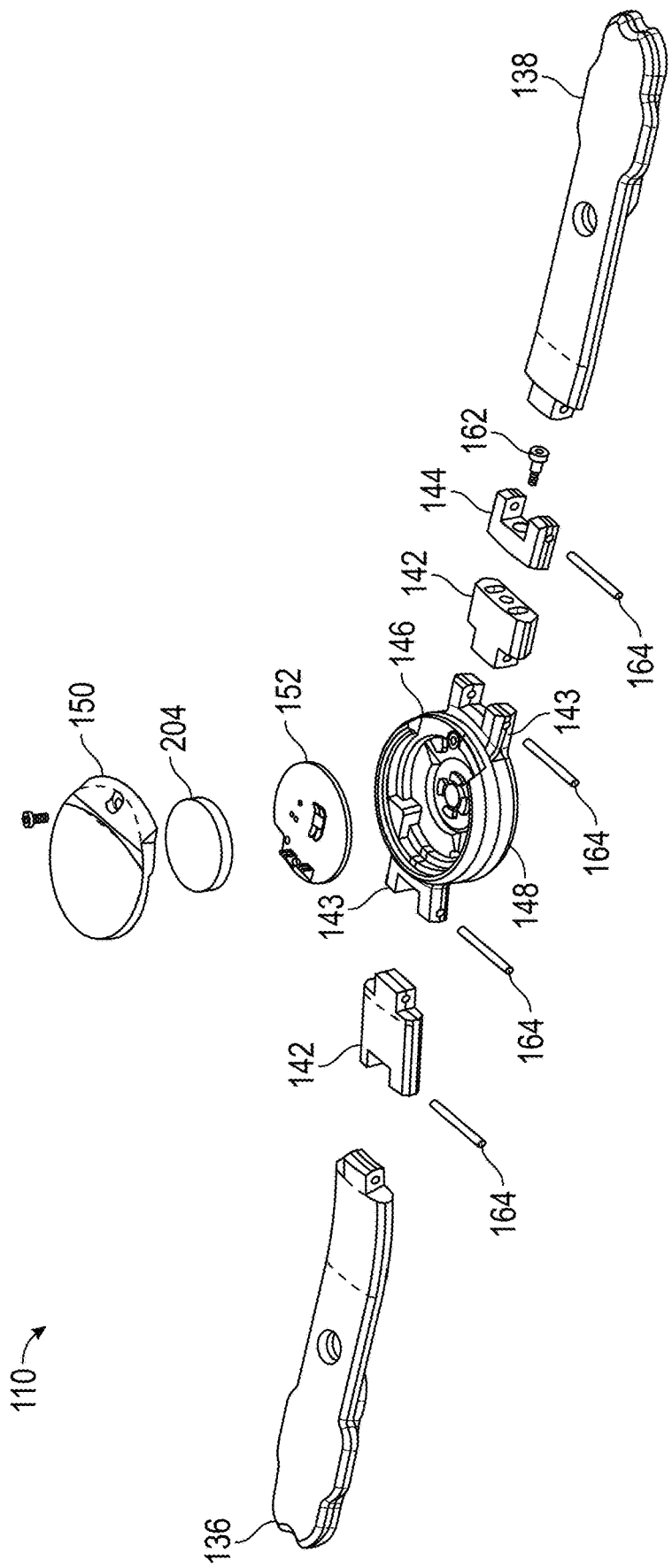
FIG. 4 is an exploded view of a goniometer in accordance with aspects of the present disclosure.

More specifically, and as best illustrated in FIG. 4, the first and second arms 128, 130 may each include an inner link 142 disposed adjacent to the respective inner ends 132, 134, and an outer link 144 disposed between the inner link 142 and the outer ends 168, 170. With reference to FIGS. 5A-C, the inner link 142 may couple to the link arm 143 in order to couple between respective arms 128, 130 and hubs 146, 148. The inner link 142 may be configured to facilitate the pivot, flex, or extension of the respective arm 128, 130 relative to the center hub 116. A pin 164 may be used to couple the inner link 142 and the link arm 143 of each arm 128, 130 to allow for the pivot, flexion, or extension of the respective arms 128, 130. The pin 164 may be disposed perpendicular to the length of the arms 128, 130.

Figure 6:
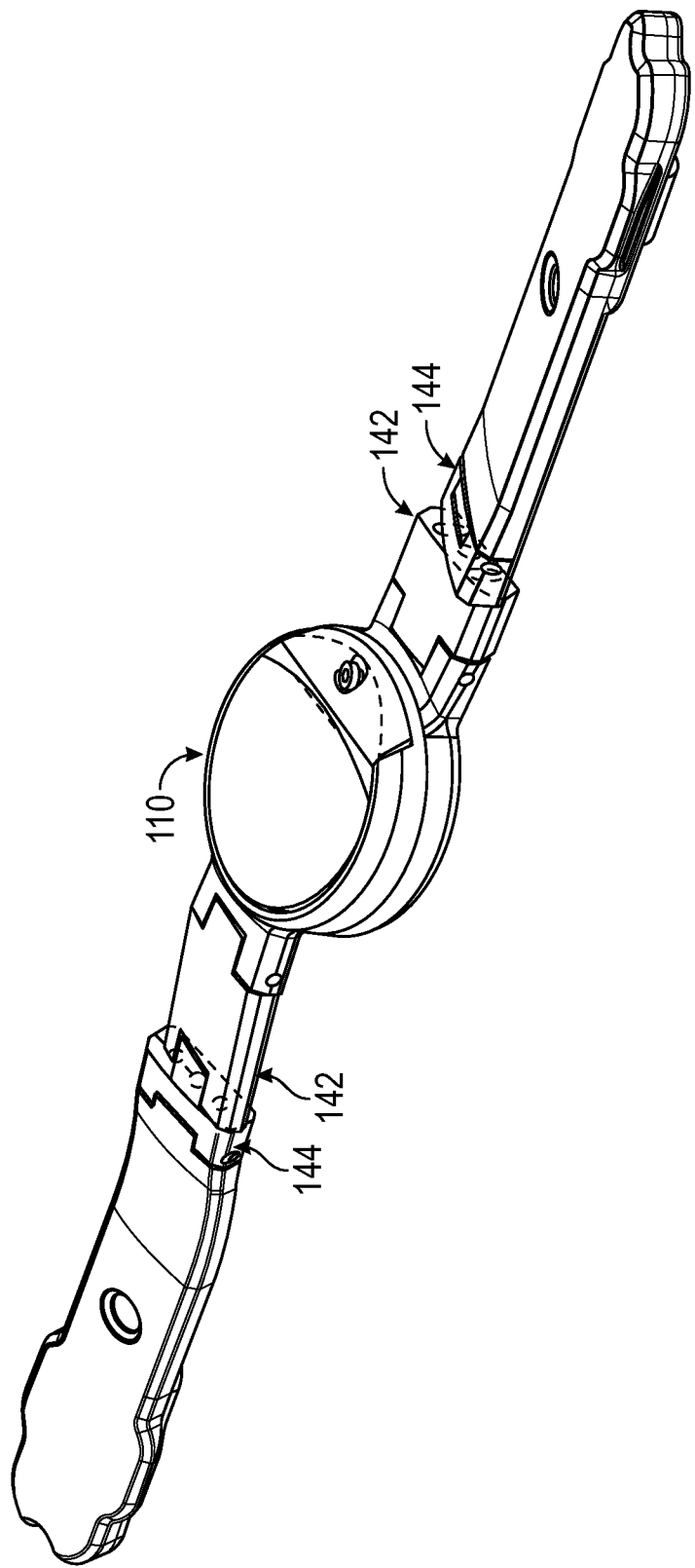
FIG. 6 is a perspective view of the goniometer with its arms twisting in accordance with aspects of the present disclosure.

The outer link 144 may couple to the inner link 142 and respective outer ends 136, 138. With reference to FIG. 6, the outer link 144 may be configured to couple to the inner link 142 to facilitate rotation of the respective arms 128, 130 relative to the center hub 116. A screw 162 may be configured to couple the outer link 144 to the inner link 142 to facilitate rotation of the respective arms 128, 130 about the screw 162, all relative to the center hub 116. The screw 162 may align parallel with the length of the respective arm 128, 130. It is to be appreciated that the first and second arms 128, 130 may rotate +/−eighteen degrees, or any other desired amount, in one or more directions. Further yet, and with reference to FIGS. 5A-C, the outer link 144 may be configured to couple to the respective outer ends 136, 138 to facilitate further pivot, flexion, or extension of the respective arms 128, 130 relative to the center hub 116. A pin 164 may be used to couple the outer link 144 and the respective outer ends 136, 138 to allow for further pivot, flexion, or extension, of the respective arms 128, 130 relative to the center hub 116. The pin 164 may be disposed perpendicular to the length of the respective arms 128, 130.

The first and second outer ends 136, 138 may comprise first and second goniometer attachments 168, 170, which may be integral with, or coupled to the respective outer ends 136, 138. It is to be appreciated the goniometer attachments 168, 170 may couple, or be integral with, the arms 128, 130 at any desired location, or in any desired configuration. The first and second goniometer attachments 168, 170 may be configured to removably couple with the attachments 118, 120. Further, each goniometer attachment 168, 170 can comprise one or more bosses 200, and one or more magnets 158 positioned next to the bosses 200 to facilitate the coupling and alignment of the goniometer attachments 168, 170 and the attachments 118, 120. The bosses 200 and magnets 158 further facilitate the alignment of the goniometer 110 relative to the attachments 118, 120. The arms 128, 130 may also include one or more arm alignment holes 140 configured to align with the attachments 118, 120, or an alignment mark on a user 102. The arms 128, 130 may further have one or more wings 202 that extend from a side 126 of the goniometer 110, such as from the first or second goniometer attachments 168, 170. The wings 202 can be formed from or coupled to the first or second goniometer attachments 168, 170. The wings 202 can be a tab or have any other desired shape. The wings 202 may be configured to assist a user in moving the arms 128, 130 of the goniometer perpendicularly relative to the attachments to facilitate uncoupling the goniometer 110 from the attachments 118, 120 without uncoupling the attachments 118, 120 from the user 102.

Figure 7A:
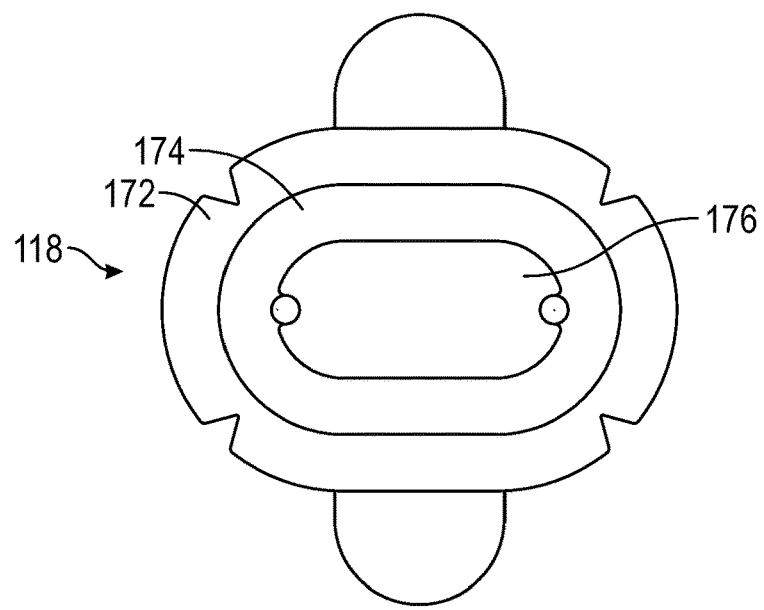
FIGS. 7A-D are top schematic views of the attachment in accordance with aspects of the present disclosure.
Figure 7B:
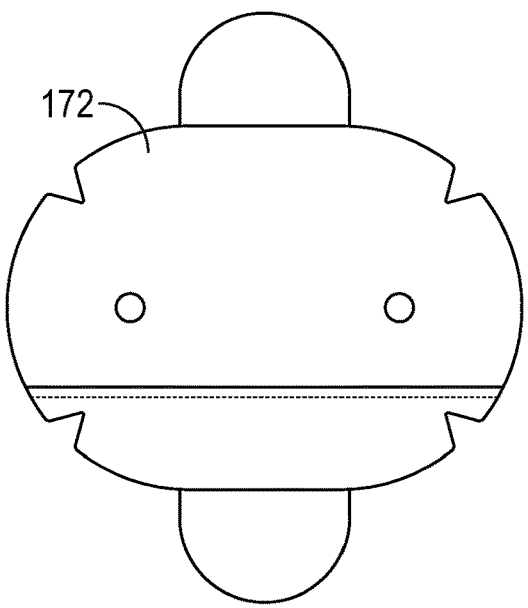
Figures 7C, 7D:
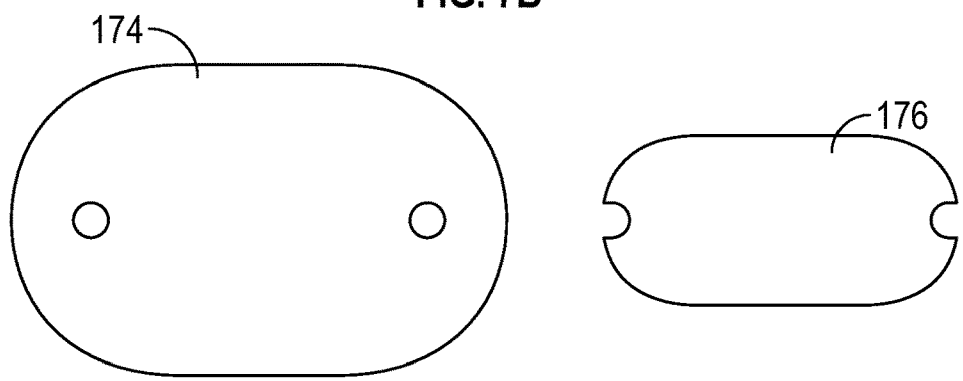
Figure 8A:
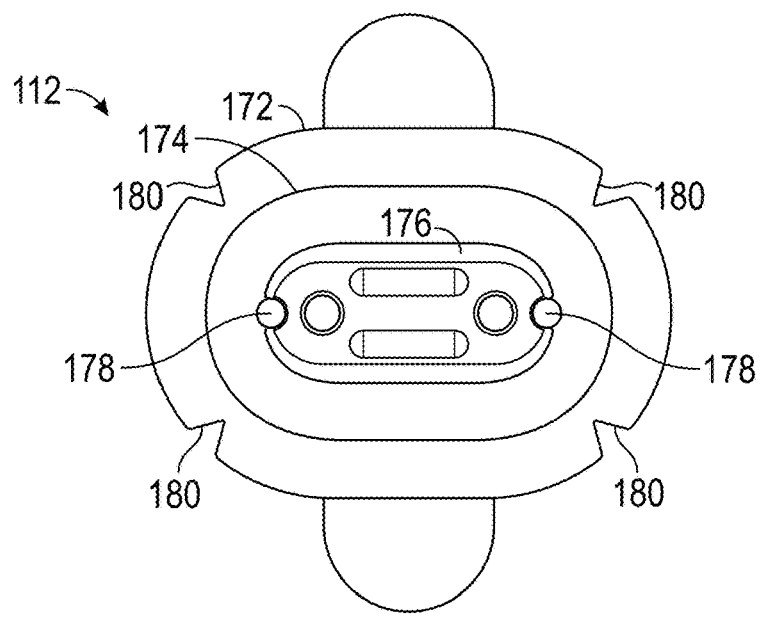
FIGS. 8A-D are views of an attachment in accordance with aspects of the present disclosure.
Figure 8B:
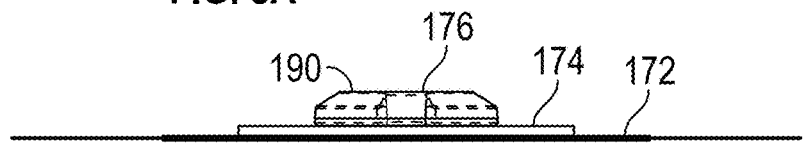
Figure 8C:
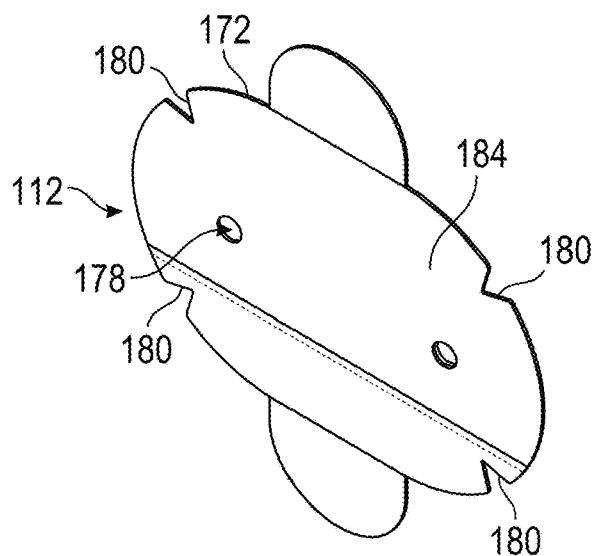
Figure 8D:
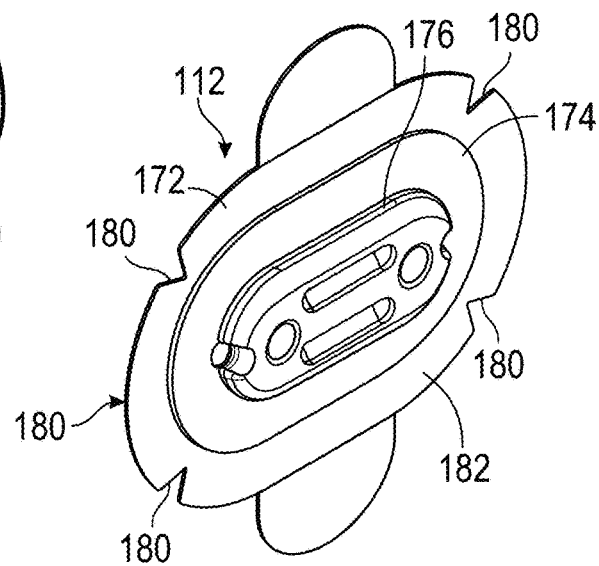
Figure 10A:
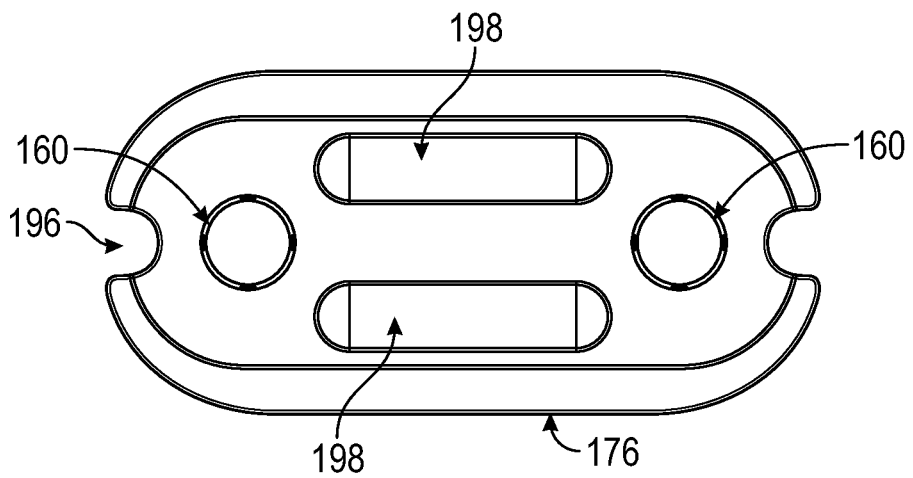
FIGS. 10A-D are views of a pod of the attachment in accordance with aspects of the present disclosure.
Figure 10B:
Figure 10C:
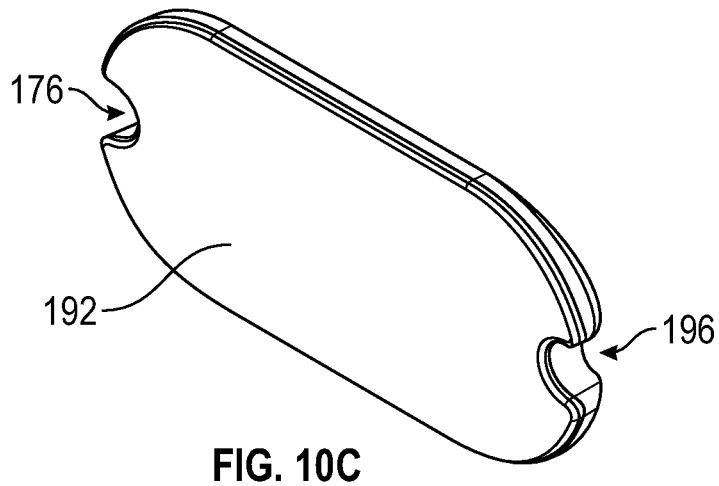
Figure 10D:
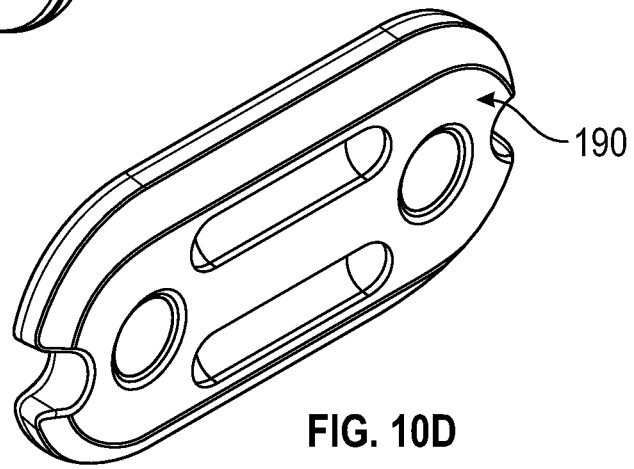

With reference to FIGS. 7-9, the attachments 118, 120 may comprise first and second layers 172, 174 and a pod 176 coupled together with one another. When coupled to one another, each of the layers 172, 174 and the pod 176 may be concentric with one another. The first attachment 118 may be the same as and interchangeable with the second attachment 120. The first layer 172, the second layer 174, and the pod 176 may be generally oval-shaped or any other desired shape. The first layer 172 may be larger than the second layer 174, and the second layer 174 may be larger than the pod 176. Further, the first layer 172 may be thinner than the second layer 174, and the pod 176 can be thicker than the first and second layers 172, 174.

The first layer 172 may have a top 182 and a bottom 184, and may be formed from a pad, coated paper, plastic, woven fabric, latex, or any other desired material. For example, the top 182 may be formed from a pad and the bottom 184 may comprise an adhesive material 236, such as a medical-grade adhesive or other suitable material. The adhesive material 236 couples to the skin of the user 102 to couple the attachments 118, 120 to the user 102. Further, the top 182 may also have an adhesive layer 194, which may be smaller in area than the first layer 172. Further, the adhesive layer 194 can be less than or equal to the area of the second layer 174. The adhesive layer 194 may be ovular in shape, and define one or more notches or voids in an outer periphery. Further, the first layer 172 can define notches 180 in an outer periphery for assisting in aligning the first attachment 118 relative to a predetermined location, or mark, on the user 102. The notches 180 can be v-shaped or have any other desired shape. Further yet, the first layer 172 may define a pair of voids or alignment holes 178, which may assist in the alignment of the first attachment 118 relative to a predetermined location, or mark, on the user 102. The alignment holes 178 and notches 180 of the first layer 172 may be the same as, or aligned with, the notches or voids of the adhesive layer 194.

The second layer 174 may have a top 186 and a bottom 188, and may be formed of a foam material or any other desired material. The second layer 174 may couple to the adhesion layer 194 of the first layer 172. To prevent uncoupling, the foam material of the second layer 174 may dampen forces between the goniometer 110 and the attachments 118, 120. The top 186 of the second layer 174 may also have an adhesive layer 195 on an upper surface 238 of the top 186, which may be smaller in area than the area of the pod 176. The adhesive layer 195 may have an ovular shape, or any other desired shape. Further, the adhesive layer 195 and the second layer 174 may have one or more holes, or one or more cutouts that may be aligned with the alignment hole 178 of the first layer 172 to align the adhesive layer 195 and the second layer 174 with the first layer 172. The adhesive layers 194, 195 can be formed of an adhesive material or any other desired coupling material, such as a hook- or a loop-type material. The first layer 172 can have a length L1 and a width W1. The second layer 174 can have a length L2 and a width W2. The adhesive layer 195 can have a length L3 and a width W3.

As illustrated in FIGS. 10A-D, the pod 176 has a top 190 and a bottom 192. The pod 176 can include one or more notches 196. For example, notches 196 can be located at opposing ends of the pod 176. The notches 196 can be used for alignment of the first coupling apparatus 112, the pod 176, or any other desired feature of the wearable device 100.

The pod 176 can include one or more magnets 160. The magnet 160 may be a neodymium magnet or any other desired magnet. The pod 176 can have a recess for housing the magnet 160. The magnet 160 can be circular or any other desired shape. Two magnets 160 can be disposed in the pod 176 at opposing ends of the pod 176. The pod 176 can be sized to be received by and detachably coupled to the upper surface 238 of the second layer 174.

More specifically, the pod 176 has an underside, such as the bottom 192, which may couple to the upper surface 238 of the second layer 174. The bottom 192 can have one or more hooks or loops, to couple to the upper surface 238. Alternatively, the upper surface 238 and the bottom 192 may comprise an adhesive material to facilitate the detachable coupling between the upper surface 238 and the pod 176. The top 190 of the pod 176 may have one or more recesses 198. The recess 198 may be ovular in shape or have any other desired shape. The recesses 198 may also have tapered edges to assist a user 102 in uncoupling from the pod 176 by moving the arms 128, 130 perpendicularly relative to the pod 176. Two recesses 198 may be formed in the pod 176 at opposing ends or sides of the pod 176.

Figure 11A:
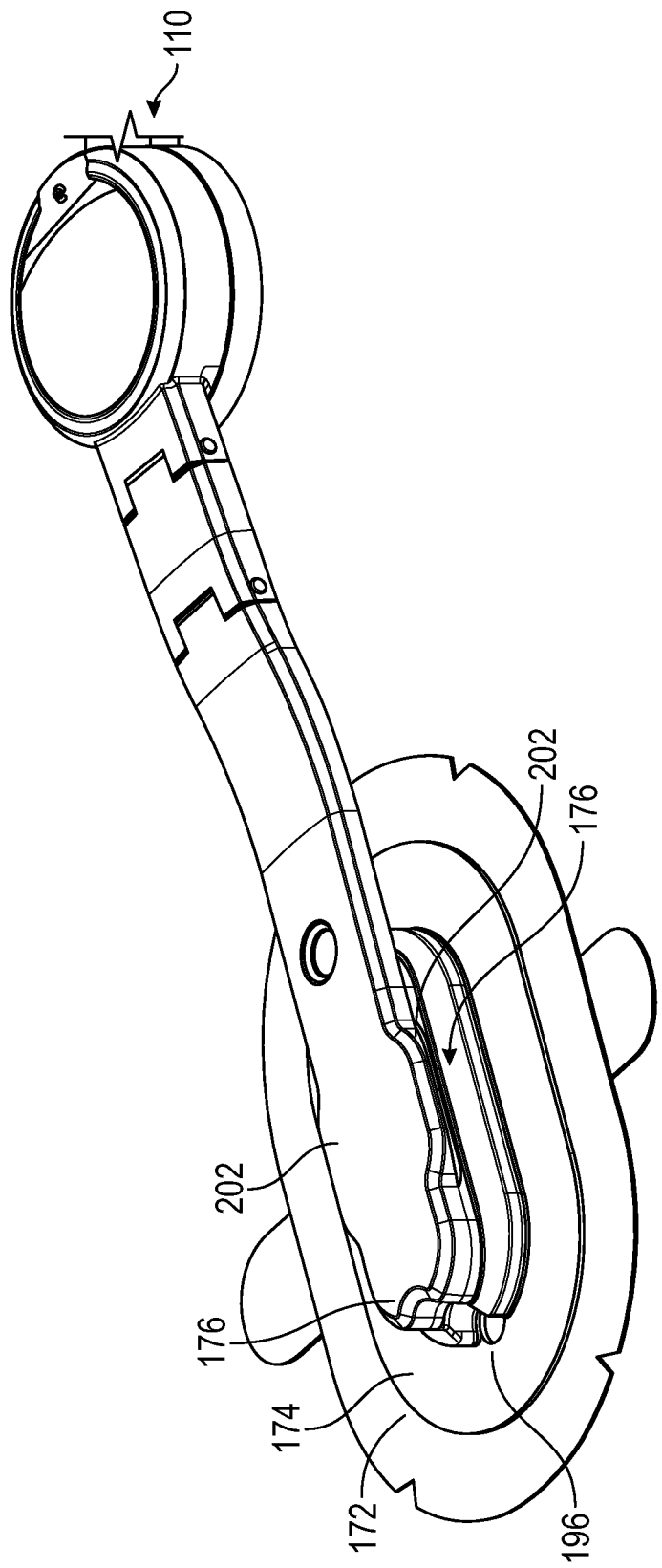
FIGS. 11A and 11B are perspective and cross-sectional views of a coupling apparatus in accordance with aspects of the present disclosure.
Figure 11B:
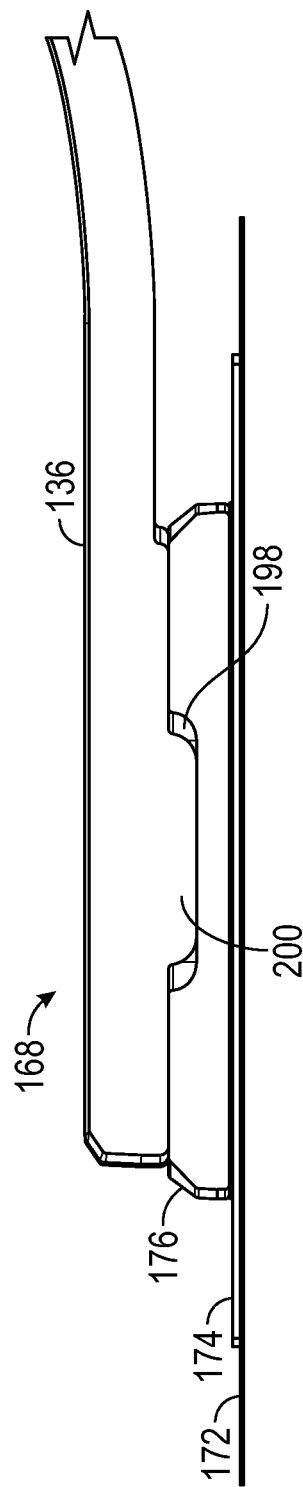
Figure 12A:
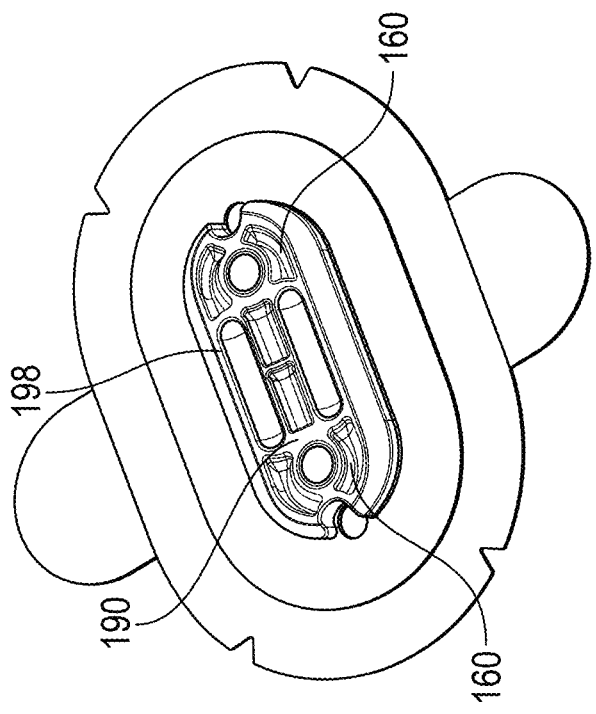
FIGS. 12A and 12B are perspective views of the attachment and a goniometer attachment in accordance with aspects of the present disclosure.
Figure 12B:
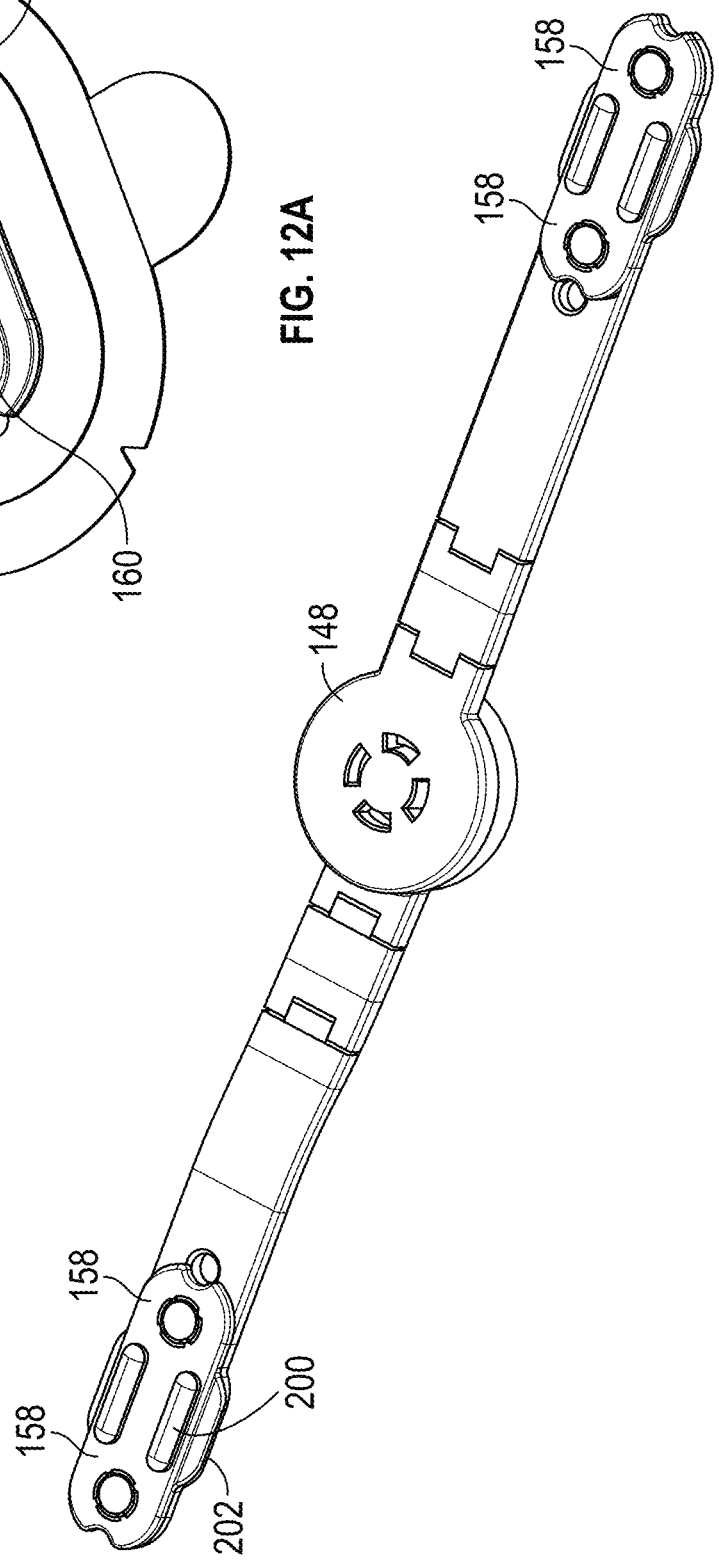

With reference to FIGS. 11-12, the recesses 198 are sized to receive the bosses 200 to align the goniometer 110 relative to the attachments 118, 120. Moreover, the recesses 198 are sized to allow slight movement of the bosses 200 to compensate for slight translational movement of the joints 128, 130 while the goniometer 110 is worn by the user 102. This movement may reduce the stress between, and prevent uncoupling of, the attachments 118, 120 to the skin, clothing, brace, or any other desired location on the user 102.

When the user 102 moves the first or second limb portions 104, 106, the first or second arms 128, 130 move or rotate with the first and second hubs 146, 148. The goniometer 110 can measure the rotation of joint 107 by measuring the angle between the first and second hubs 146, 148. To achieve this, and with reference to FIGS. 4, 13-15, the center hub 116 defines an opening for receiving and containing a printed circuit board (PCB) 152, a sensor 216, a retaining ring 154, a magnet 156, or any other components of the goniometer 110 which cooperate with one another to measure relative angular movement between the arms 128, 130. More specifically, the first and second hubs 146, 148 may define the opening of the center hub 116.

For enclosing the opening, a cover 150 may be attached to the center hub 116, and more specifically to the first hub 146. The cover 150 can be detachably coupled to the first hub 146 or any other desired location. The cover 150 can also be configured to inhibit movement of the PCB 152 and other components located within the center hub 116. For example, when the cover is closed, a bottom portion of the cover 150 may apply direct or indirect pressure to the PCB 152. The cover 150 may have a snap mechanism 226, such as a finger snap or any other desired mechanism, configured to attach and detach the cover to the center hub 116.

The magnet 156 may couple to the second hub 148, and the sensor 216 also disposed in the center hub 116 is configured to detect rotation of the magnet 156. The sensor 216 can be configured to measure the rotation of the magnet 156 to a sensitivity up to one-hundredth of a degree, or to any other desired sensitivity.

Figure 13:
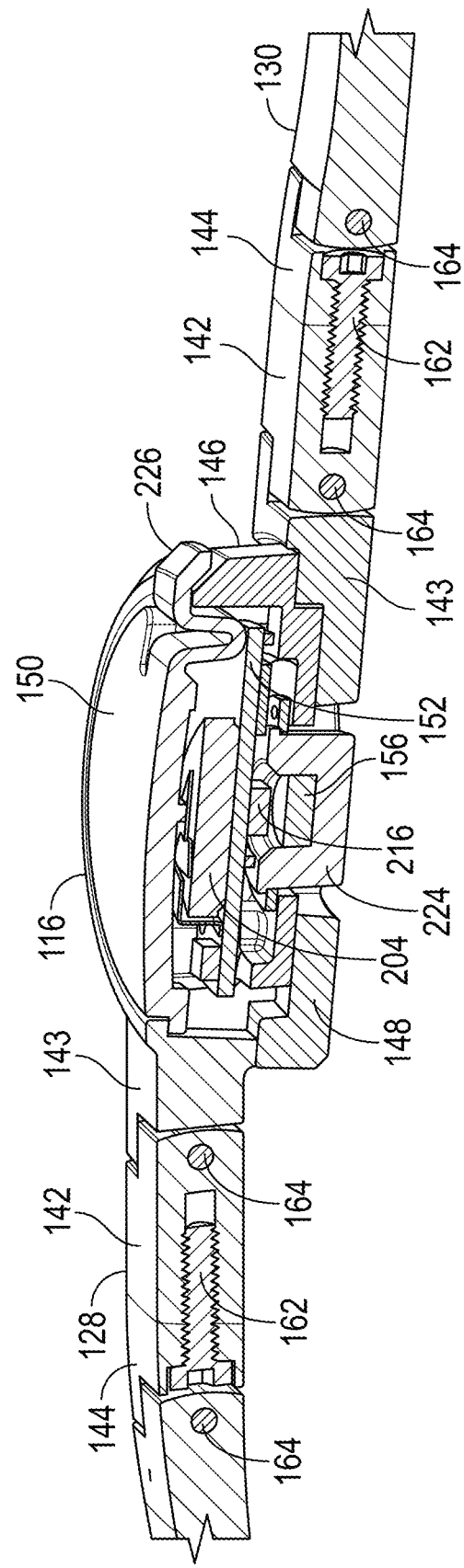
FIG. 13 is a cross sectional view of the goniometer in accordance with aspects of the present disclosure.
Figure 14A:
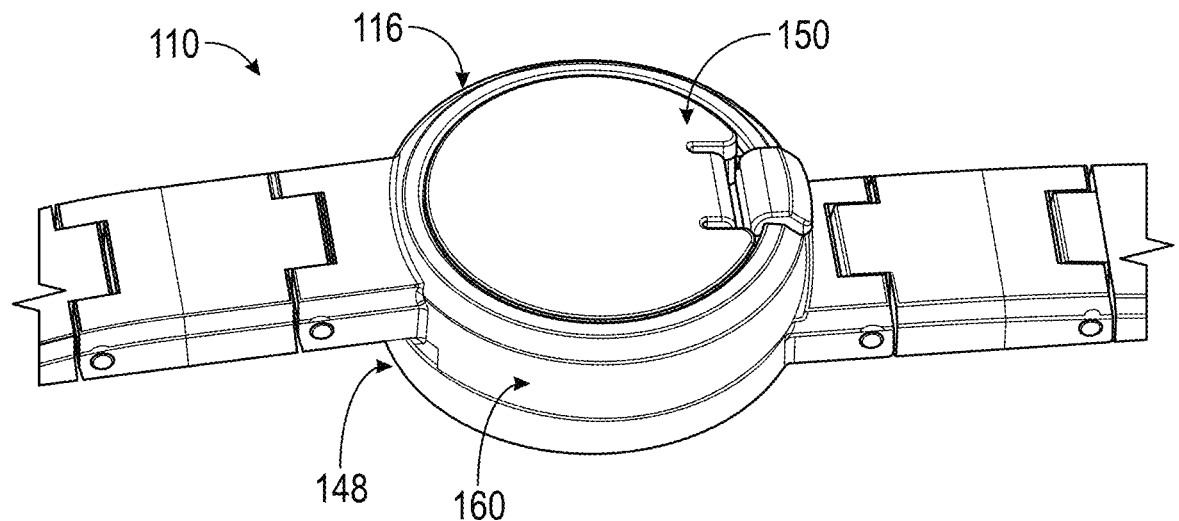
FIGS. 14A-C are perspective and top views of a center hub of the goniometer closed, open, and with components removed in accordance with aspects of the present disclosure.
Figure 14B:
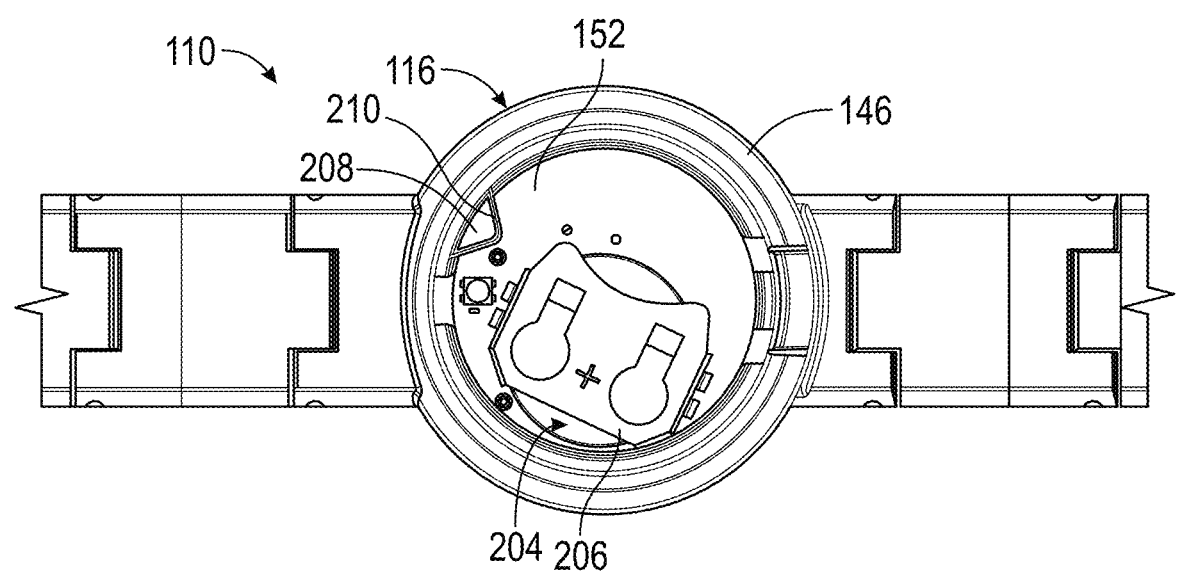
Figure 14C:
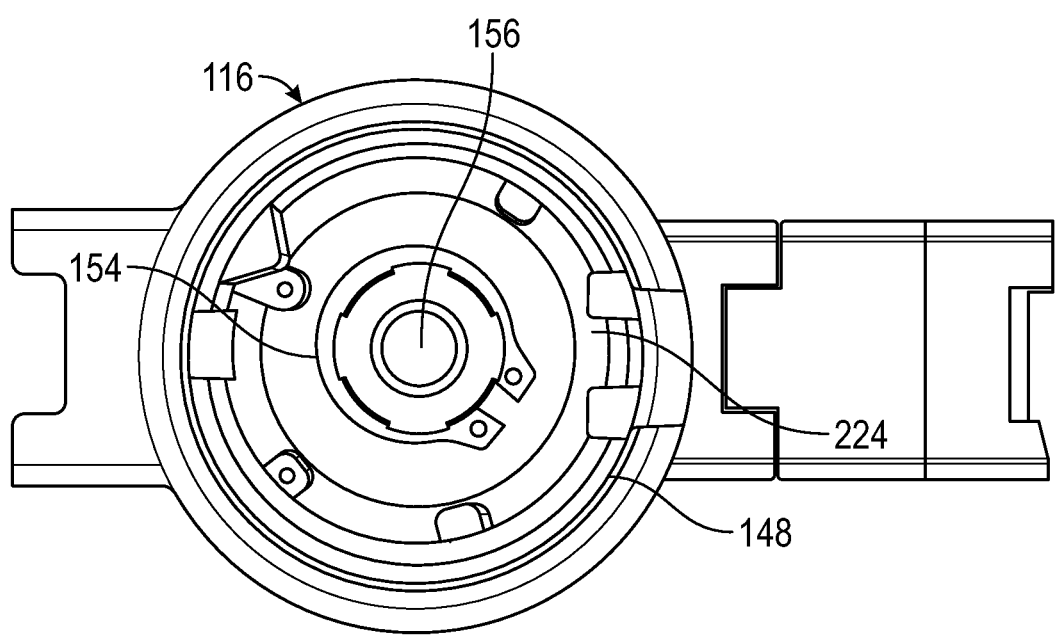

As illustrated in FIGS. 13-14C, the center hub 116 includes the first hub 146 positioned rotatably above the second hub 148. An outward notch 208 may be coupled to the first hub 146, or any other desired location. The outward notch 208 may be formed with the first hub 146 or attached to the first hub 146. The PCB 152 may be removably disposed in the center hub 116. The PCB 152 may have an inward notch 210. The outward notch 208 may be configured to couple with the inward notch 210 to align the sensor 216 and the magnet 156. The alignment can restrict movement of the PCB 152 within the center hub 116.

When the cover 150 is removed, the PCB 152 may be accessed. FIG. 14B illustrates a battery housing 206 coupled to the PCB 152. The battery housing 206 may be attached to a top side 212 of the PCB 152. The battery housing 206 may be formed of conductive metal or any other desired material. When the cover 150 is attached to the first hub 146, the cover 150 may apply pressure to the battery housing 206, which may secure PCB 152 within the center hub 116. A battery 204 may be detachably coupled to the battery housing 206. The battery 204 may be a lithium ion battery or any other desired battery or power source. The battery housing 206 may have tabs or any other desired contact points for conduction with the battery 204. The battery 204 may be removed from the battery housing 206 to turn the goniometer 110 off or for replacement of the battery 204. For example, when the cover 150 is opened or removed from the first hub 146, the PCB 152 may be removed from the center hub 116 and the battery 204 may be replaced. To maintain calibration of the goniometer 110 after a battery replacement, the inward notch 210 of the PCB 152 is configured for receiving the outward notch 208 of the first hub 146.

In FIG. 14C, the cover 150 and the PCB 152 are removed from the center hub 116. As shown, the second hub 148 may include a magnet housing 224. The magnet housing 224 may be located in the center of the second hub 148 or any other desired location. The magnet housing 224 may be coupled to the PCB 152 using a weld, an adhesive, a tack, or any other desired attachment. The magnet housing 224 may be configured to receive the magnet 156. The magnet 156 may be configured to have north and south polarity within the center hub 116 or any other desired polarity. The magnet housing 224 may include a lip at a top of the magnet housing 224 or have any other desired configuration. The retaining ring 154 may be configured to couple the magnet 156 to the second hub 148. The retaining ring 154 may be coupled to the second hub 148 around the magnet housing 224. For example, the retaining ring 154 may be positioned between the lip or top of the magnet housing 224 and the second hub 148. The retaining ring 154 may secure the magnet within the magnet housing 224. The retaining ring 154 may move with the second hub 148 and the magnet 156 as the second hub 148 rotates with the second arm 130.

Figure 15A:
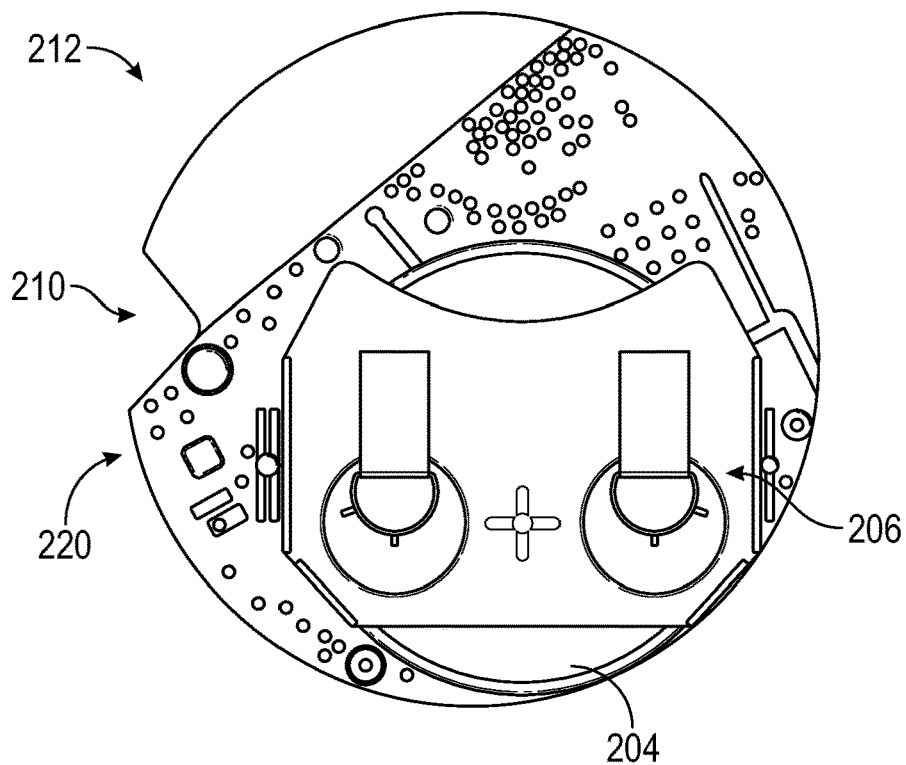
FIGS. 15A and 15B are top and bottom views of a printed circuit board (PCB) in accordance with aspects of the present disclosure.
Figure 15B:
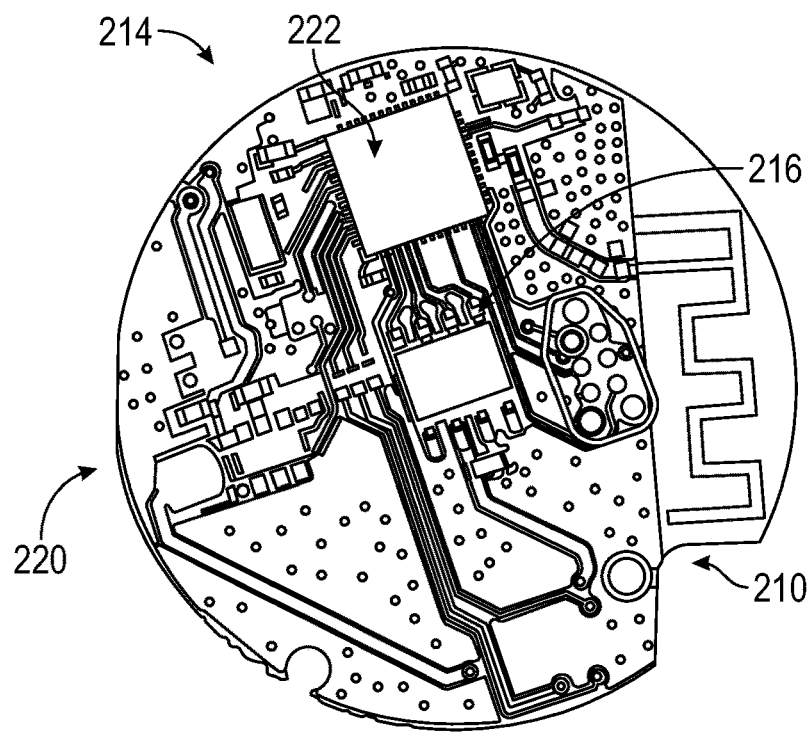

FIG. 15A illustrates the top side 212 of the PCB 152. As described above, the battery housing 206 may be attached to the top side 212. FIG. 15B illustrates a bottom side 214 of the PCB 152 in accordance with aspects of the present disclosure. The PCB 152 includes components coupled to the bottom side 214. The components may comprise a circuit 220 including resistors, LEDs, transistors, capacitors, inductors, transducers, diodes, switches, the sensor 216, a transmitter 222, or any other desired component. The components may be attached to the PCB 152 using a surface mount method, a through-hole method, or any other desired method. The PCB 152 may include additional and/or fewer components and is not limited to those illustrated in FIGS. 15A and B.

The circuit 220 may be configured to generate an electrical signal based on the rotation of the magnet 156. The circuit 220 may be configured to transmit the electrical signal in real time. The circuit 220 may transmit the electrical signal. For example, a transmitter 222 may be coupled to the PCB 152 and configured to transmit an electrical signal based on the rotation of the magnet 156 to an external device. The transmitter 222 may include wired or wireless transmission, such as Bluetooth™, WiFi, NFC or any other means or method of desired transmission. The external device may be a mobile phone, a computer, a tablet, or any other desired device. The external device may have a user interface. The user interface may be configured to receive the electrical signal and display data obtained from the electrical signal. The data may include the angle of the joint 107, or any other desired information.

The user interface may include an app that receives the data, manipulates the data, records the data, and displays aspects of the data. For example, the app may display the angle of the joint 107 of a user 102, a history of the angle of the joint 107, duration of the angle, or any other desired information, such as a measurement of the angle in real time.

The sensor 216 may be a Hall Effect sensor, or any other desired sensor (e.g., a magnetic position sensor AS5601 using internal MEMS Hall Effect sensors). The sensor 216 may be coupled to the PCB 152 or any other desired device. The sensor 216 may be coupled to the bottom side 214 of the PCB 152 at a location directly above the magnet 156 when the PCB 152 is disposed within the center hub 116. The PCB 152 and the sensor 216 may rotate with the first hub 146 and the first arm 128. The magnet 156 may rotate with the second hub 148 and the second arm 130. The design of the wearable device 100, including the configuration of the sensor 216 and the magnet 156, may improve the accuracy of the measurements of the angle of the joint 107.

Figure 16A:
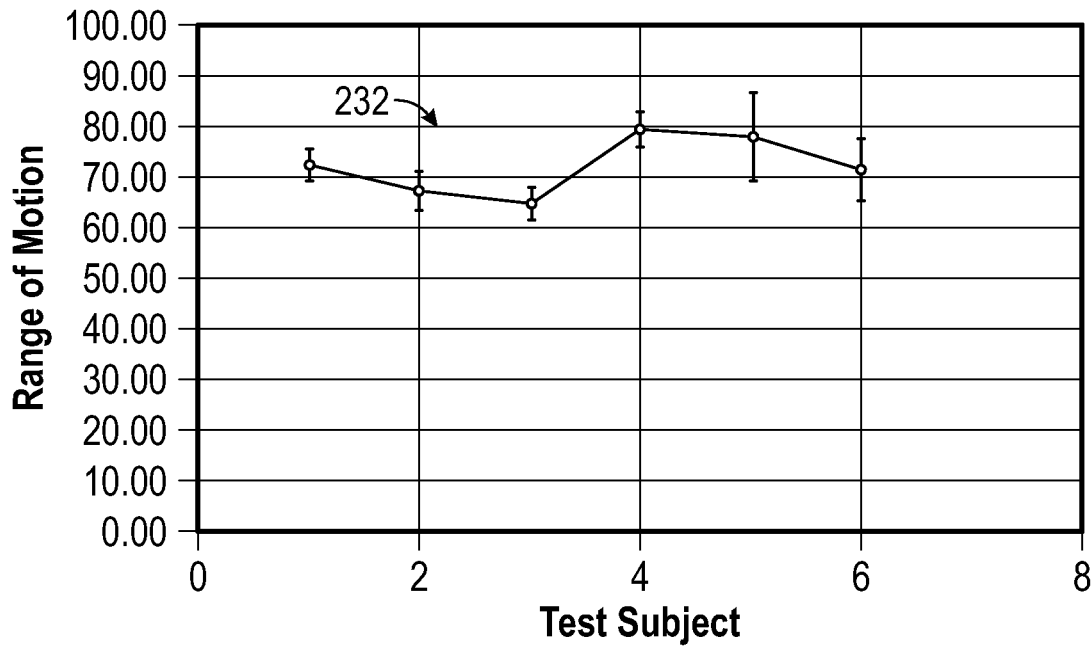
FIGS. 16A and 16B are graphs illustrating test data in accordance with aspects of the present disclosure.
Figure 16B:
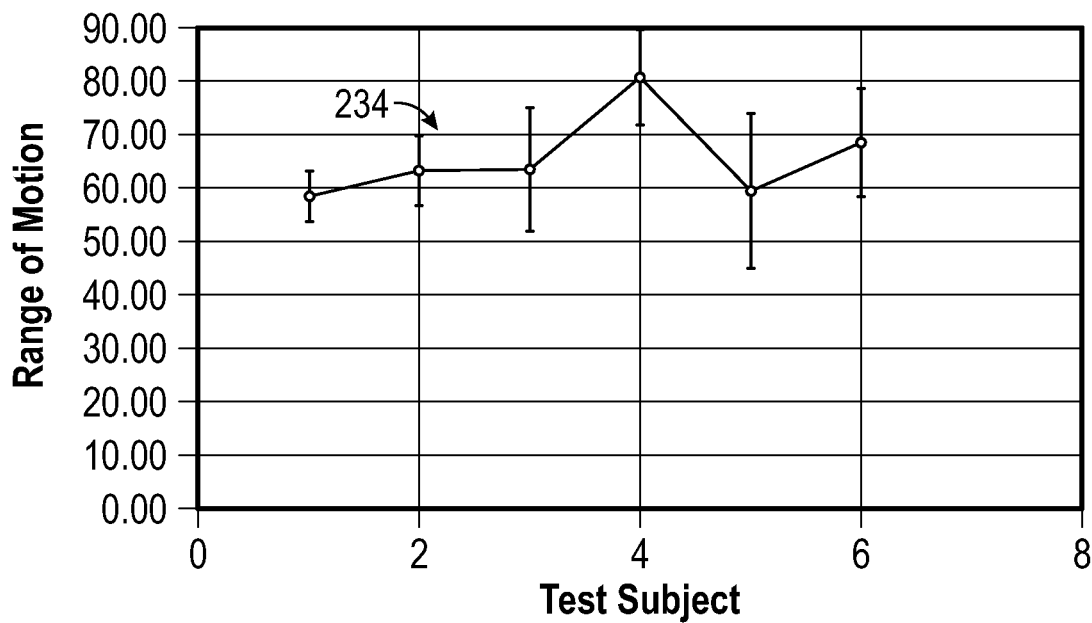

FIG. 16A is an exemplary graph 228 with line 232 depicting, while the wearable device 100 is attached to the user 102, the accuracy of measurements of angles of the joint 107 by the wearable device 100. FIG. 16B is an exemplary graph 230 with line 234 depicting the accuracy of measurements of angles of the joint 107 by a different measurement device attached to a user using Velcro™ straps. The standard deviation of the measurements made by the different measurement device shown by line 234 is greater than the standard deviation of the measurements made by the wearable device 100 shown by line 232. Users, such as clinicians or patients, are able to more accurately initially place and realign the first and second attachments 118 and 120 of the wearable device 100 as compared to using the Velcro™ straps. The configuration of the first and second arms 128, 130 of the wearable device 100 to fit different users may increase accuracy of the measurements. The configuration of the components, including the PCB 152, the sensor 216, and the magnet 156 within the center hub 116 of the wearable device 100 may further increase accuracy of the measurements. The wearable device 100 may be configured to measure the angle of the joint 107 up to an accuracy of measurement up to a one hundredth degree. The different measurement device may have an accuracy up to five degrees. In other words, the measurements taken by the different measurement device may have an accuracy of about +/−five degrees, such as about +/11 degree, or even +/−about 0.01 degree from the actual angle of the joint 107.

Figure 17:
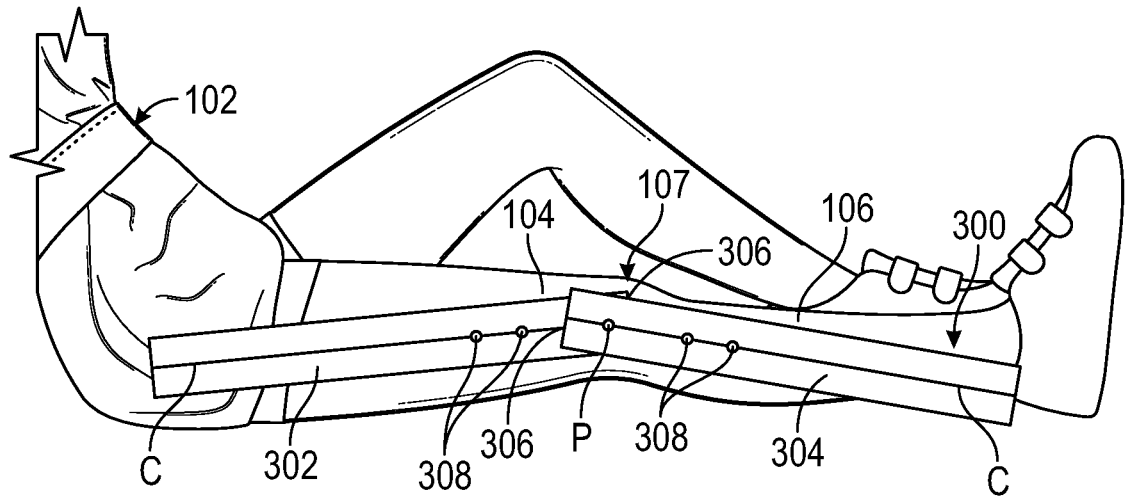
FIG. 17 is a perspective view of the alignment device, with the alignment device shown aligned relative to the center of the joint of the user.
Figure 18:
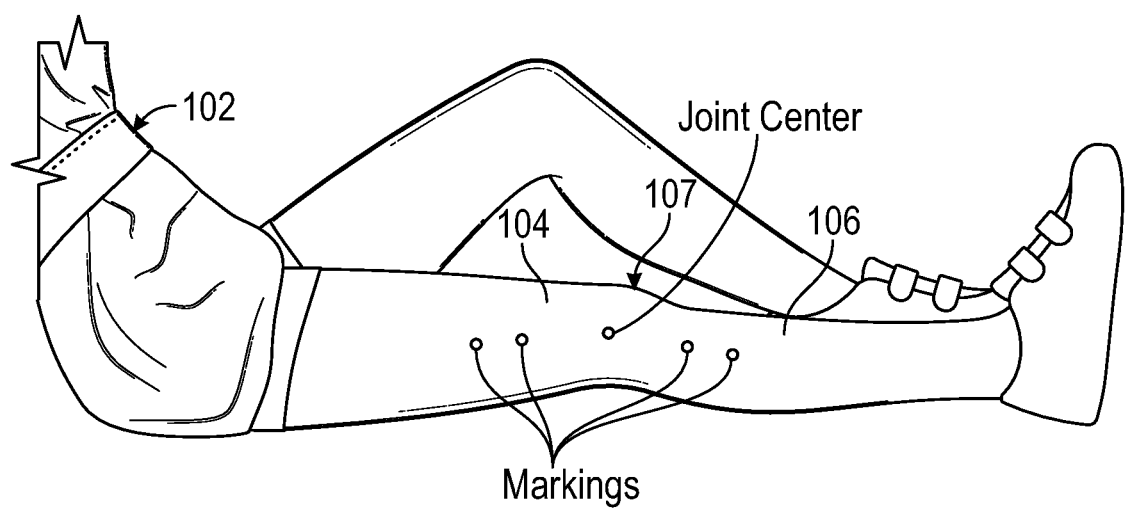
FIG. 18 is a perspective view of the user illustrating the markings on the skin of the user at the center of the joint, and on the opposing limb portions.
Figure 20:
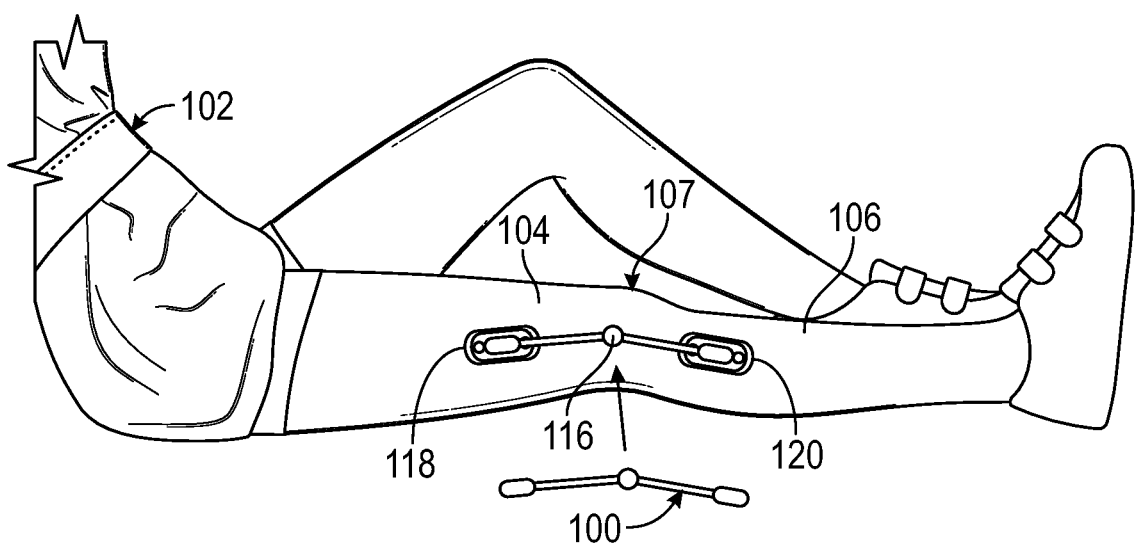
FIG. 20 is a perspective view illustrating the wearable device being coupled to the attachment, and aligned relative to the center of the joint.

With reference to FIGS. 17 and 18, the alignment device 300 may be used to assist a clinician to align the wearable device 100 (see FIG. 20) on opposing limb 104, 106 portions of the joint 107 of the user 102 relative to a center of the joint 107. Properly aligning the wearable device 100 relative to the joint 107 facilitates greater accuracy and precision of the measurements made with the wearable device 100. Hence, the need for a device, such as alignment device 300, to assist in aligning the wearable device 100 relative to the joint 107 of a patient 102.

The alignment device 300 comprises a first segment 302 and a second segment 304 pivotably coupled to the first segment 302 at a pivot point P. More specifically, the segments 302, 304 each have a coupling end 306 where the segments 302, 304 pivotably couple to one another at the pivot point P. Moreover, the pivot point P is spaced adjacently and equidistant from each coupling end 306 of the segments 302, 304. Further yet, when the segments 302, 304 are pivotally coupled, center axes C of each segment 302, 304 intersect at the pivot point P.

Figure 19:
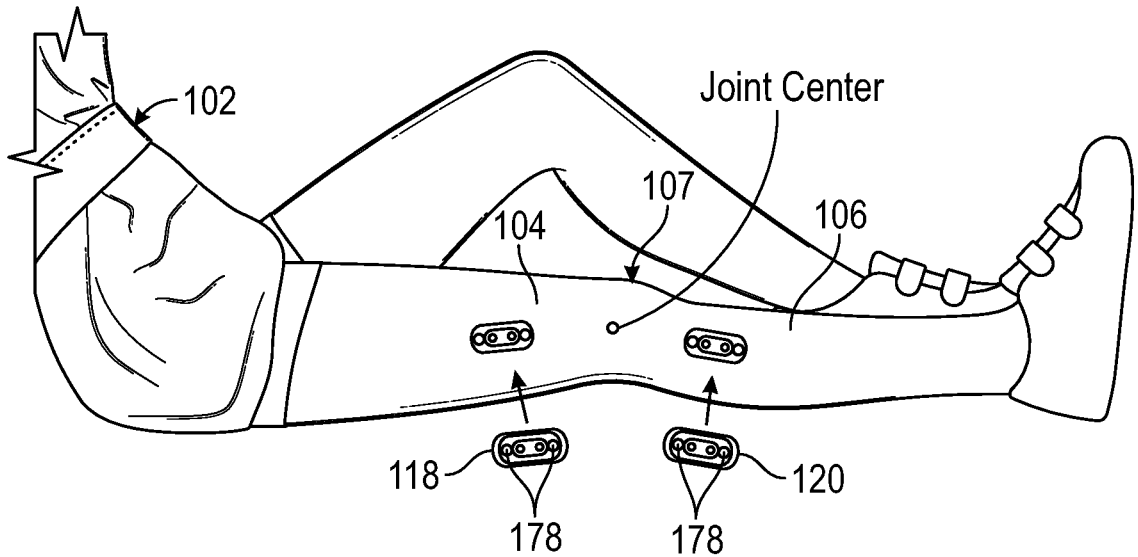
FIG. 19 is a perspective view illustrating the attachments being aligned with the markings on the opposing limb portions.

The alignment device 300 further includes voids 308 defined by each segment 302, 304, and the voids 308 facilitate the marking of the skin of the user 102 during use of the alignment device 300. The voids 308 are spaced equidistant on each segment 302, 304 from the pivot point P, and the spacing between, and size, of each void 308 is commensurate with the spacing between, and size, of each alignment hole 178 of the attachments 118, 120 (see FIGS. 19 and 20). Further yet, when the attachments 118, 120 are coupled to the goniometer attachments 168, 170, the spacing between, and position of, each void 308 and the pivot point P is commensurate with the spacing between the center hub 116 and the alignment holes 178 of the attachments 118, 120.

Using the alignment device 300, the clinician may locate the center of the joint 107 of the user 102, and then position the pivot point P at the center of the joint 107. When the joint 107 of the user 102 is a knee, the clinician may locate the lateral epicondyle of the knee, and position the pivot point P adjacent to the lateral epicondyle. With the pivot point P positioned adjacent to the lateral epicondyle, the clinician may centrally position each segment 302, 304 adjacent to the opposing limb portions 104, 106 of the joint 107. The clinical may rely on the center axes C of each segment 302, 304 to assist in centrally aligning with the segments 302, 304 to the opposing limb portions 104, 106. With reference to FIGS. 17 and 18, with the segments 302, 304 centrally aligned with the opposing limb portions 104, 106, the clinician may use the voids 308 to mark the skin of the user 102. Thereafter, and with reference to FIGS. 19 and 20, the clinician may coaxially align the alignment holes 178 of the attachments 118, 120 with the markings on the skin of the user 102 to facilitate the alignment, and coupling to the user 102, of the wearable device 100 relative to the center of the joint 107. Further, the clinician may use pegs to assist in aligning with the attachments 118, 120 coaxially with the marks.

Figure 21:
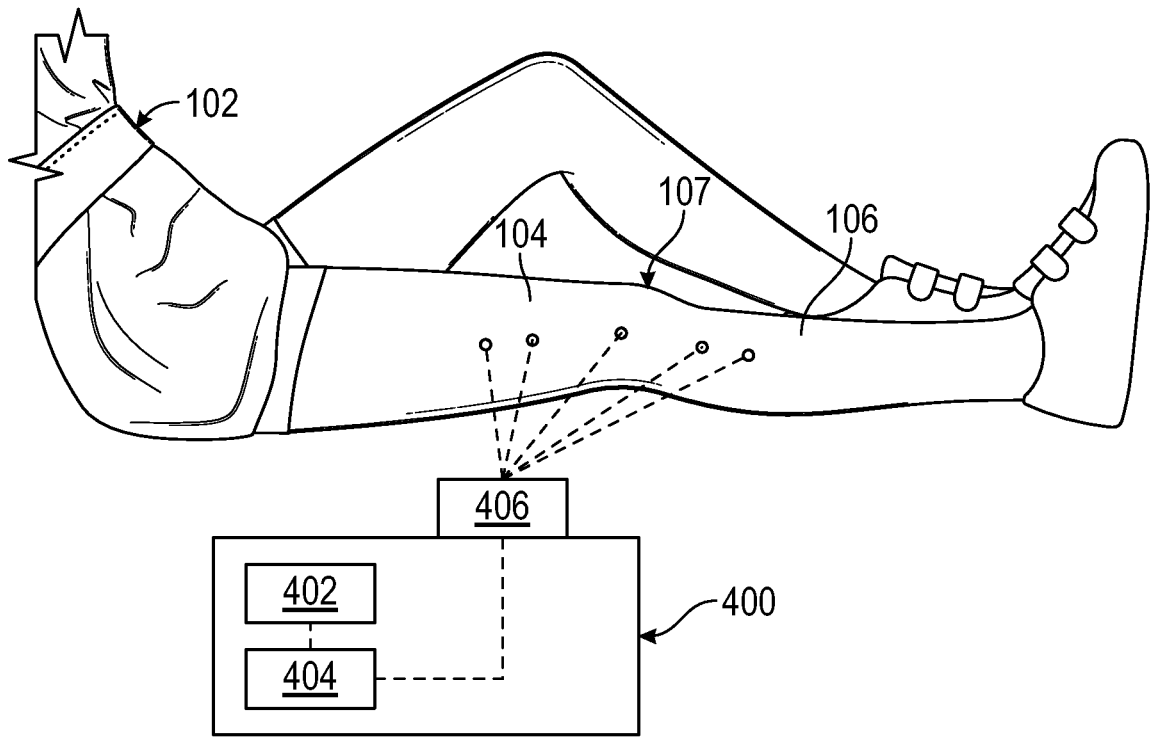
FIG. 21 is a perspective view illustrating an alternative embodiment of the alignment device, and illustrating the light beams at the center of the joint and on the opposing limb portions, which are configured to assist the clinician in aligning the attachments and wearable device relative to the center of the joint.
Figure 22:
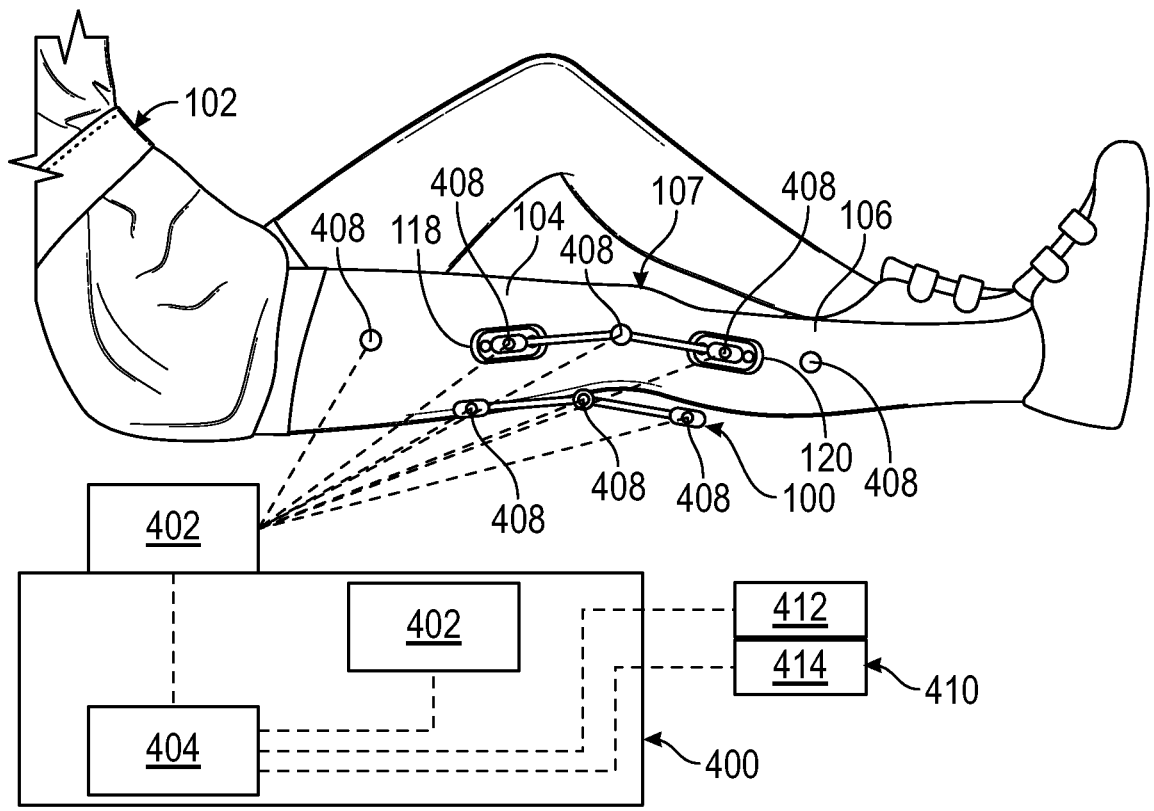
FIG. 22 is a perspective view illustrating yet another alternative embodiment of the alignment device, and illustrating the diodes at the center of the joint, on the opposing limb portions, and on the wearable device.
Figure 23A:
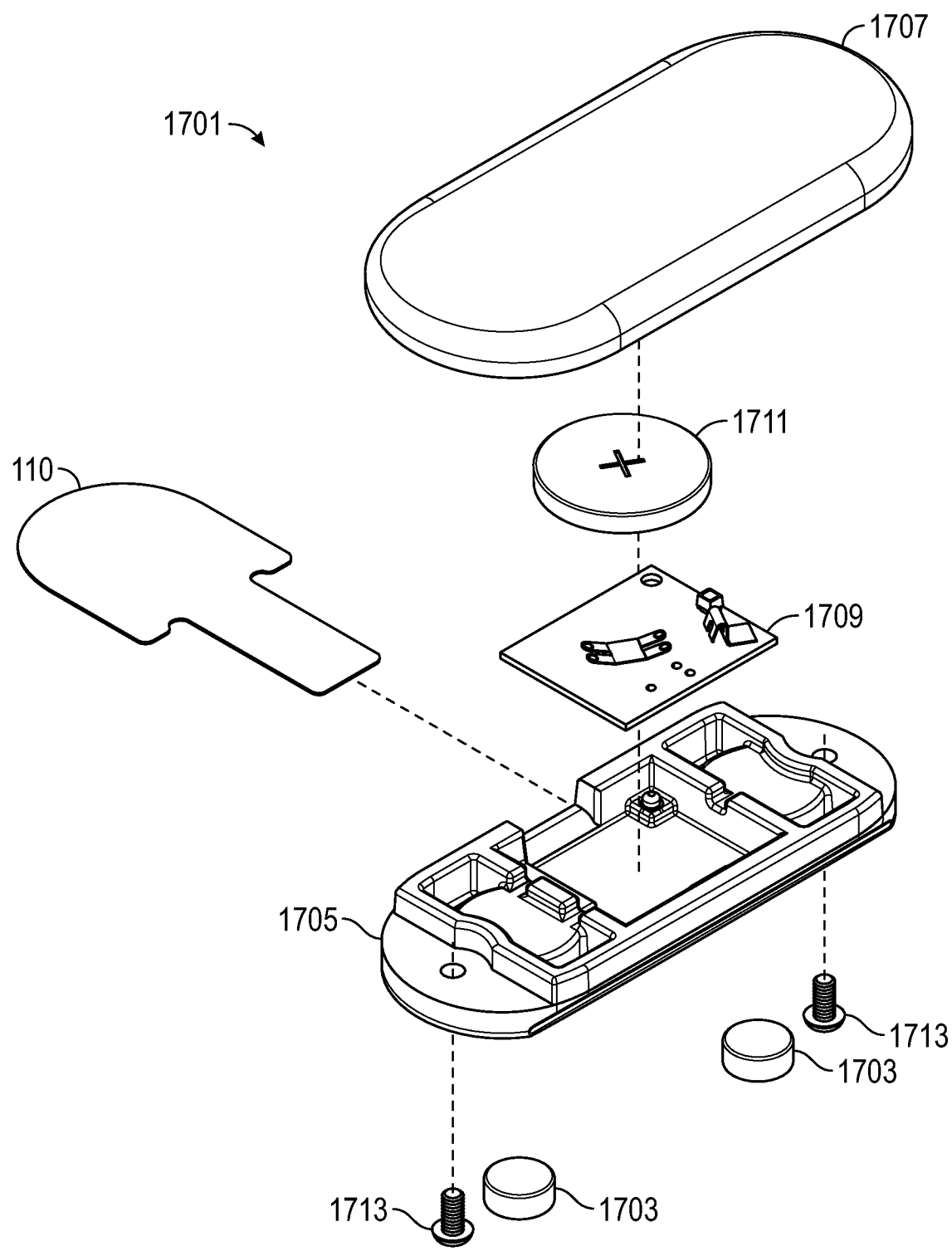
FIGS. 23A-23E are various views of an embodiment of a pedometer that may be coupled to the goniometer.
Figure 23B:
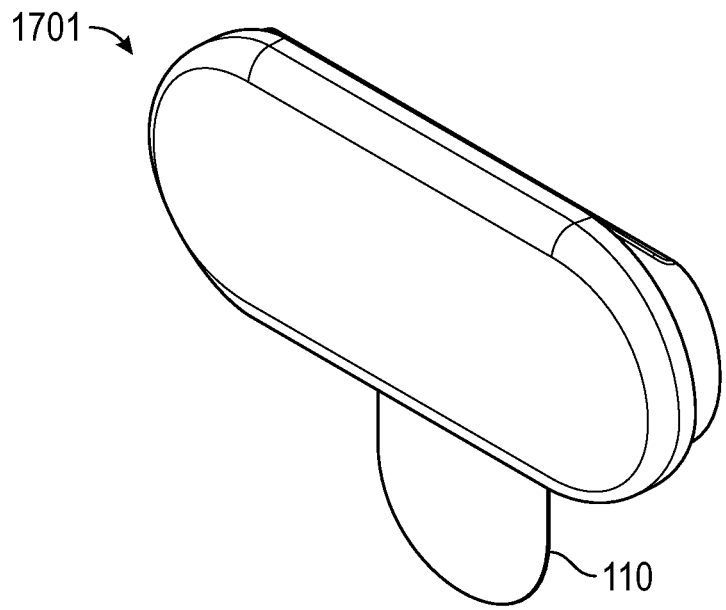
Figure 23C:
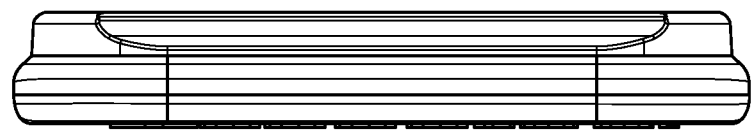
Figure 23D:
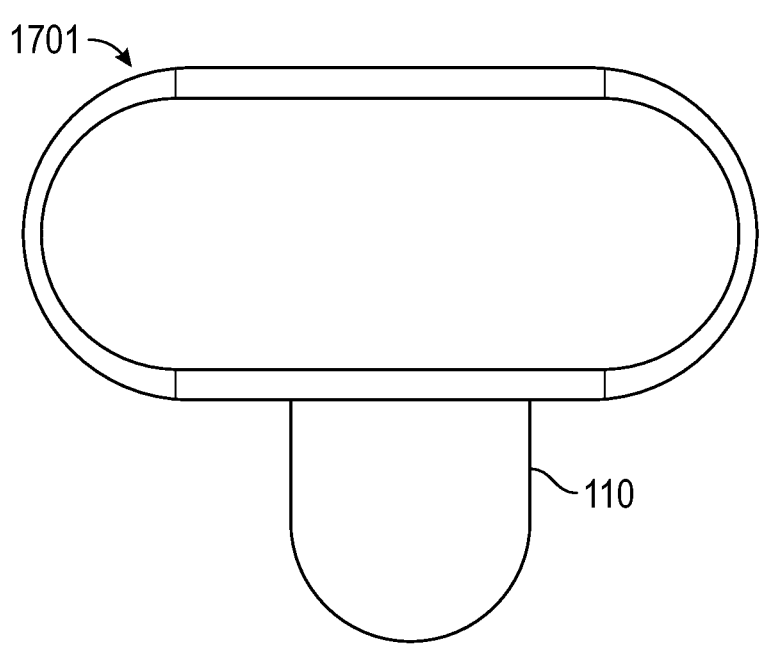
Figure 23E:
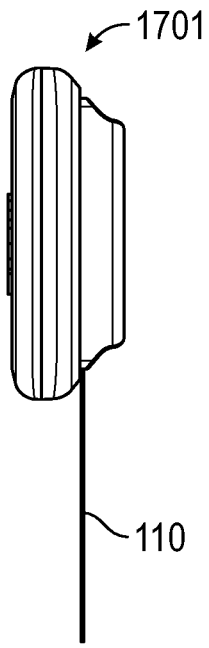

Alternatively, and with reference to FIGS. 21 and 22, an alignment device 400 may be used to assist a clinician to facilitate the alignment of the wearable device 100 relative to a center of the joint 107 of the user. More specifically, alignment device 400 may rely on data from an imaging device 402 of the joint 107 to assist the clinician in positioning the wearable device 100 on the user 102. The imaging device 402 may be an x-ray, ultrasound, any other imaging device capable of providing image data in 2D, 3D or 4D to the alignment device 400, or any other imaging device. A processor 404 of the alignment device 400 receives and processes the image data from the imaging device 402, and the processor 404 facilitates communication from the alignment device 400 to the clinician for the proper positioning of the attachments 118, 120, or the wearable device 100.

In one embodiment, and with reference to FIG. 21, the alignment device 400 may include one or more lasers 406 that produce a light beam. In this embodiment, the processor 404 may communicate with the lasers 406 to cause the lasers 406 to be positioned such that light beams causes spots of light on the skin of the user 102 on the center of the joint 107 and on opposing limb portion 104, 106. The spacing between, and size of, the spots of light are commensurate with the spacing between, and size of, each alignment hole 178 of the attachments 118, 120. The clinician may rely on the spots to align the wearable device 100 to center of the joint 107. Alternatively, the clinician may mark the locations of the spots of light on the skin, similar to the markings used with alignment device 300, and rely on the markings to align the wearable device 100 to the center of the joint 107. Further yet, the wearable device 100 may have indicia which the clinician may align with the light beams to facilitate alignment of the wearable device 100. In yet another alternative, the light beam may create an outline of the wearable device 100 on the skin of the user 102, where the outline may be commensurate to a perimeter of the wearable device, and may be used to properly align the wearable device 100 to the center of the joint 107.

In another embodiment of the alignment device 400, and with reference to FIG. 22, to assist the clinician in aligning the wearable device 100 relative to a center of the joint 107 of the user 102, the imaging device 402 may communicate with diodes 408 positioned on the user 102 and/or the wearable device 100. The diodes 408 may provide position data to the processor 404 such that the processor 404 may communicate with, and position, the lasers 406 to assist the clinician in the positioning of the attachments 118, 120. Alternatively, with the position data of the diodes 408, the processor 404 may communicate, to the clinician, with a clinician communication device 410, to assist in the alignment of the wearable device 100. Further yet, the wearable device 100 may also have diodes 408, which may communicate with the imaging device 402. Relying on position data of the diodes 408 from the imaging device 402, the processor 404 may cause the speaker 412 or the display 414 to provide respective audio or image outputs to communicate instructions, to the clinician, to facilitate the alignment of the wearable device 100. For example, the speaker 412 may provide audio guidance to the clinician, such as "move wearable device 5 mm to the left," to assist in the positioning of the wearable device 100. In another example, the display 414 may provide visual guidance to the user 102 on the location of the wearable device 100, and instructions for adjusting its position to achieve proper alignment. The display 414 may be a monitor, or iPad, or any other device for providing an image to the user, such as 3D googles. Of course, any of the above techniques could be used in combination with one another to assist the clinician to properly align the wearable device 100.

FIGS. 23A-23E depict an embodiment of an ambulation monitor or pedometer 1701. Versions of the pedometer 1701 can count the number of steps that a user takes, such as a daily count of steps post-operatively. Such a device can be carried by the user or attached to the user or to a peripheral of the user, such as the goniometer 110. The pedometer 1701 is operational to track steps of the user even if the user requires a walker or other assistance device.

In some versions, the pedometer 1701 can include the ability to attach to the magnets of the goniometer 110 to ensure accurate tracking of all steps of the user. The pedometer 1701 can include metallic elements that are magnetically attracted to the magnets of the goniometer 110. Alternatively, additional magnets 1703 mounted to the pedometer 1701. Embodiments of the pedometer 1701 can further include a body 1705, a removable cap 1707, a circuit board 1709 including one or more sensors (e.g., a motion sensor such as an accelerometer, mechanical sensor or other electromechanical sensor), a battery 1711 and fasteners 1713.

Figure 24:
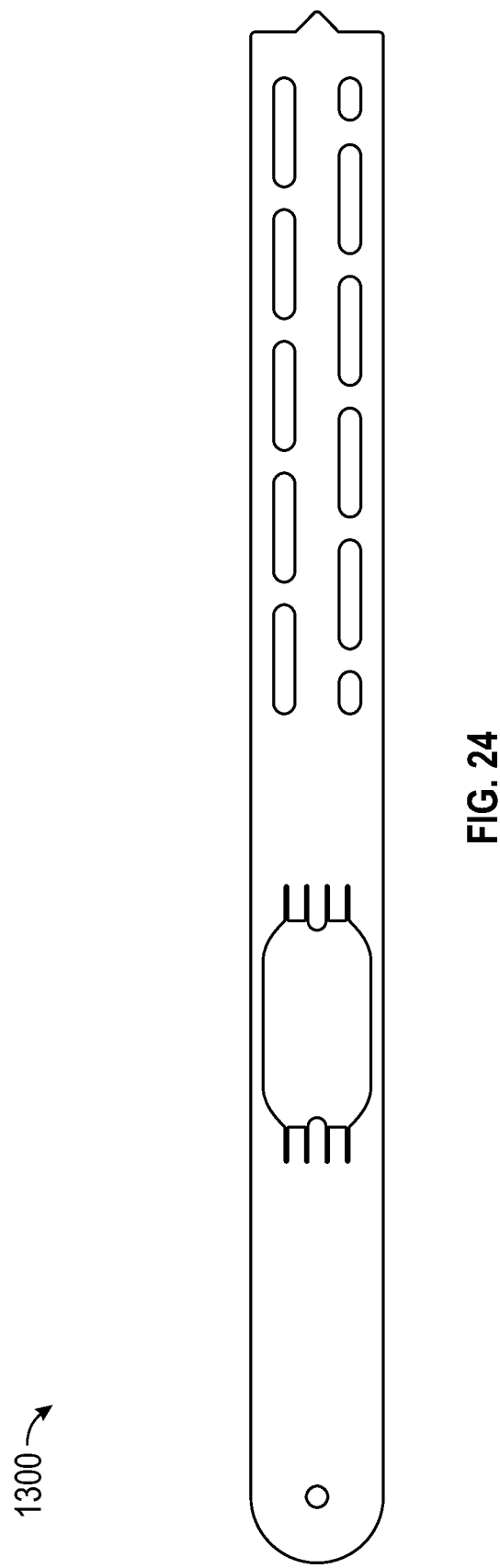
FIG. 24 is a plan view of another embodiment of an alignment device.
Figure 26:
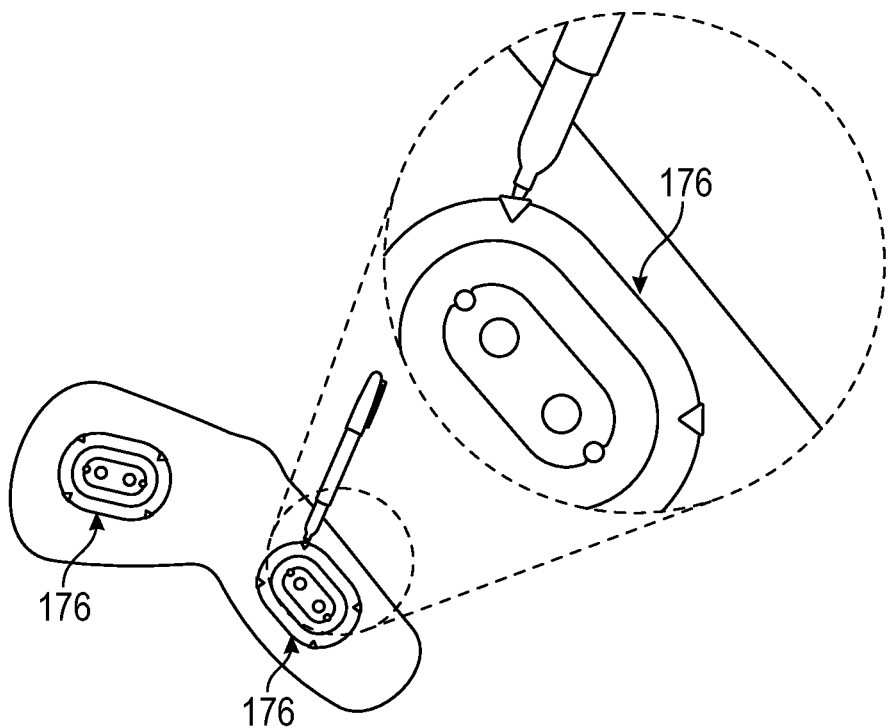
Figure 27:
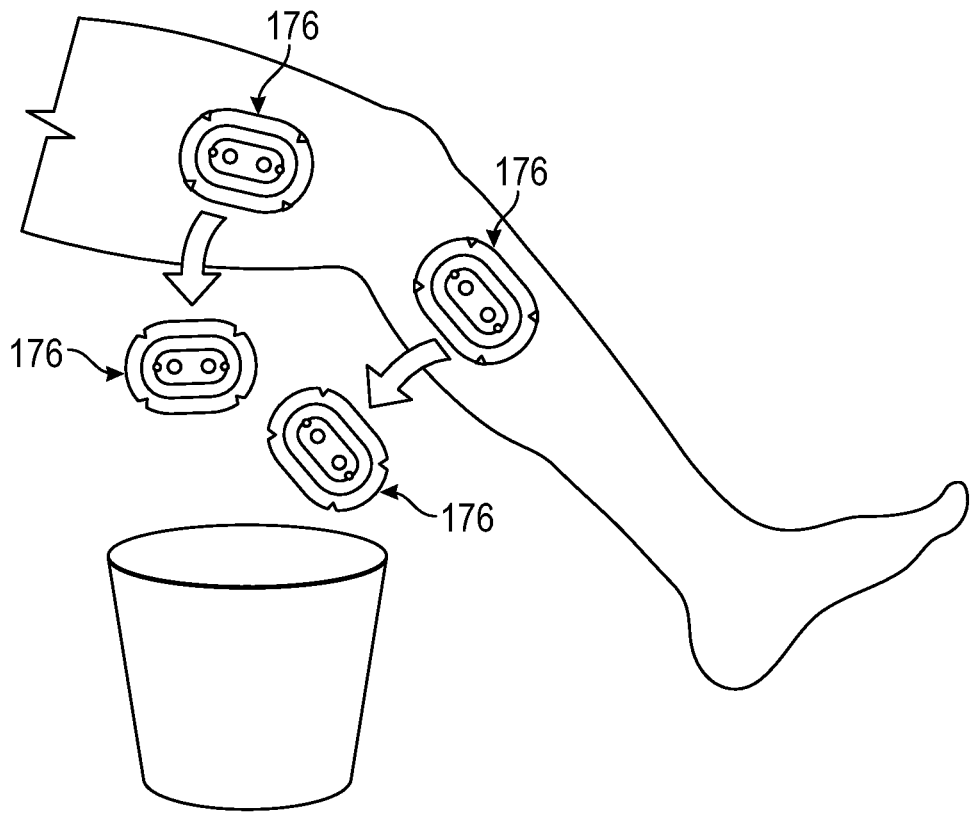
Figure 28:
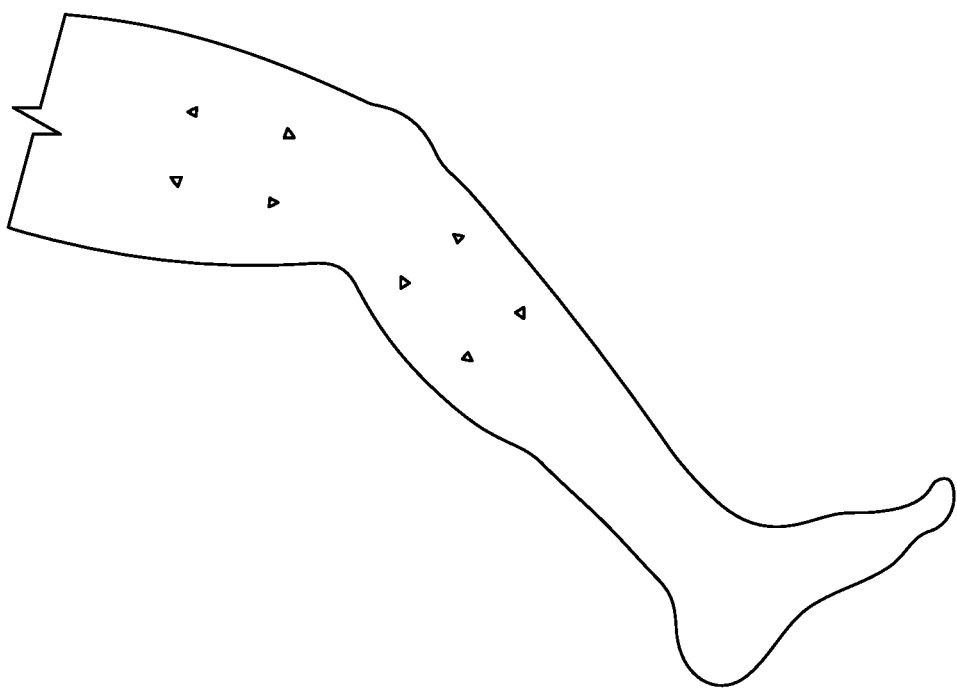

FIG. 24 is a plan view of another embodiment of an alignment device 1300. Alignment device 1300 can be used in manners that are similar to the previously described alignment devices.

FIGS. 25-34 are schematic sequential images of an embodiment of alignment and installation method. As shown in FIG. 25, the patient or user can change their own pods 176. Alternatively, another person can help the user change their pods 176. Although these images are shown for the user's right leg, the actions are mirrored for the user's left leg.

Before either pod 176 is removed (FIG. 26), a permanent ink marker can be used to mark the user's skin with four marks (e.g., triangles) inside the four V-shaped notches on each of the user's current pods 176. A total of eight triangular marks can be made, including four marks on the pod attached to the user's upper leg and four marks on the pod attached to the user's lower leg. These marks can be used to correctly position the new pods 176.

Starting at the edge of one of the pods 176 (FIG. 27), the adhesive portion of the pod can be gently peeled away and off of the user's skin. Repeat for the second pod 176, and discard both of the old pods 176. After removing both old pods 176 from the user's skin (FIG. 28), the user can wait 24 hours before putting on new pods 176. This gives the skin time to "air out" and restore itself after being covered for a week. The area may be cleaned with mild soap to avoid removal of the ink markings. If one or more of the markings are fading, they can be re-marked before they disappear entirely.

Figure 29:
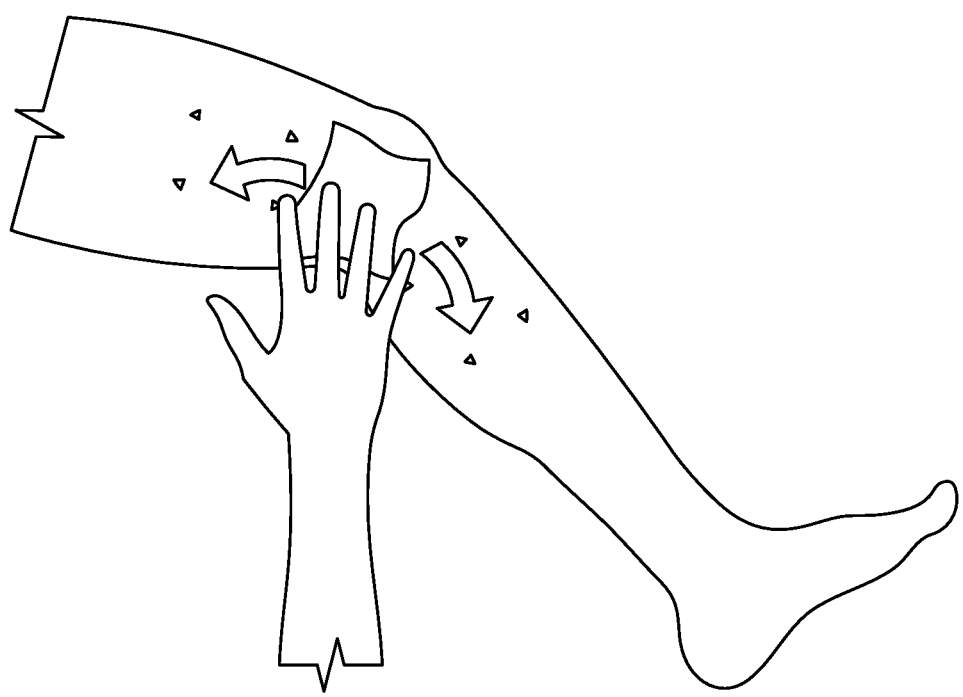
Figure 30:
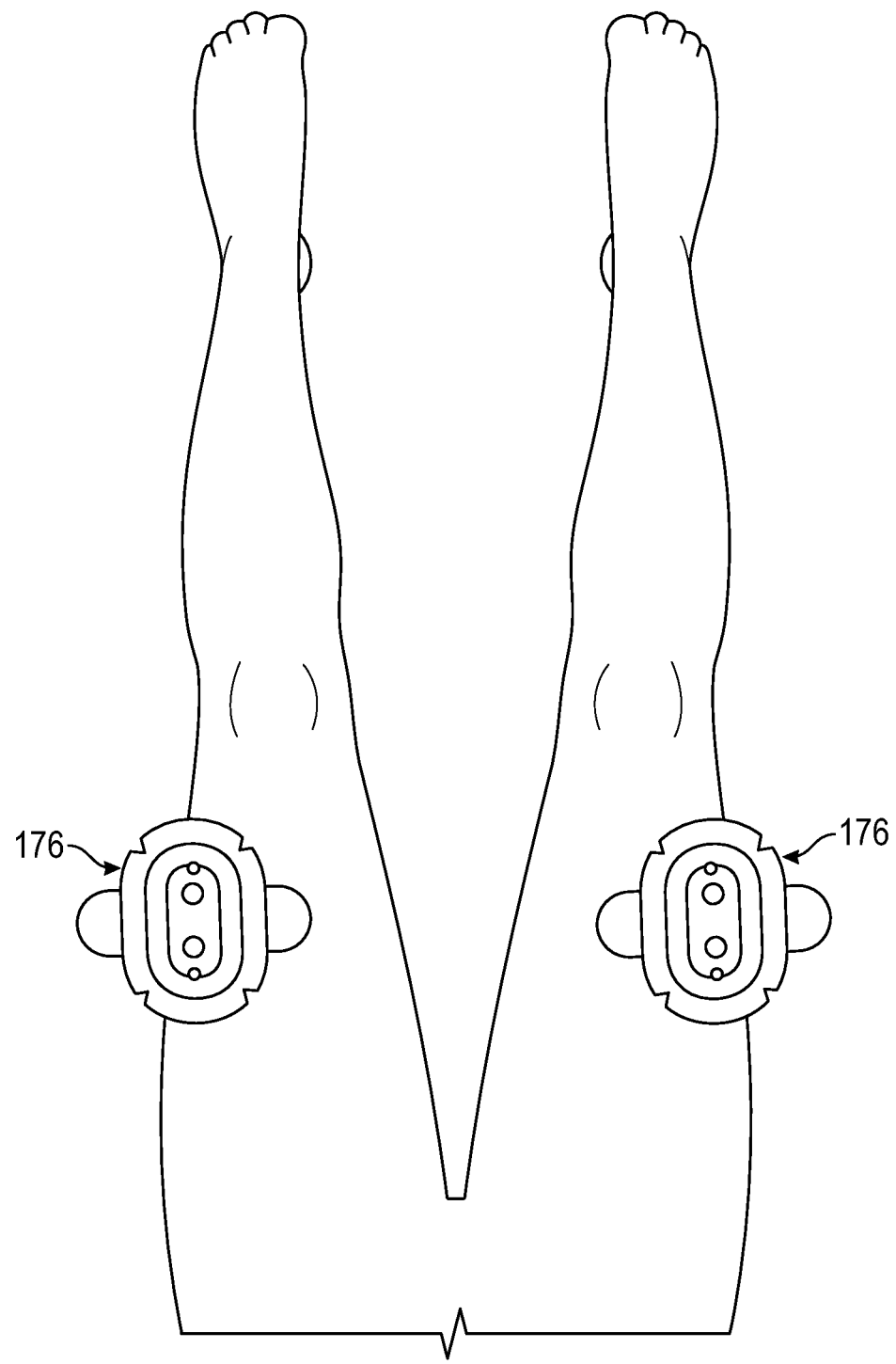
Figure 31:
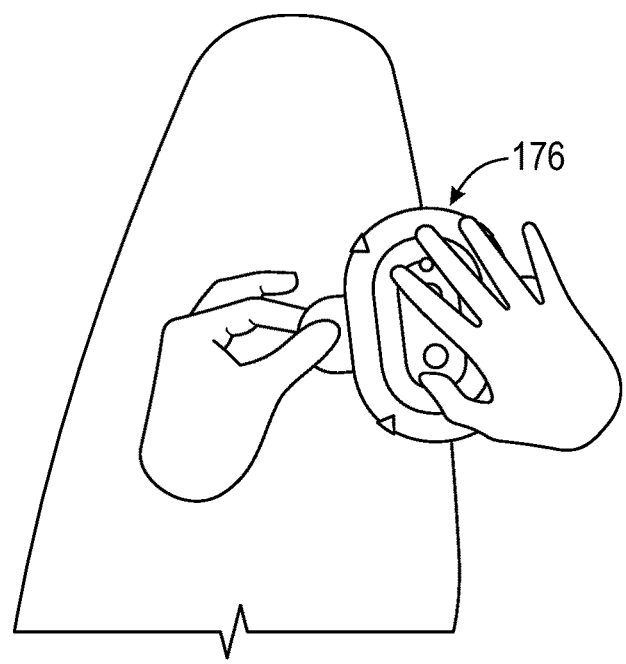

In FIG. 29, the area is cleansed with a simple hand soap, rinsed and dried. In FIG. 30, two new pods 176 are removed from their packaging and correctly oriented such that the "1" tab is pointing toward the center of the user, and the "2" tab is pointing outward away from the user. In FIG. 31, the V-notches in the pod are aligned with the triangles drawn on the user's upper leg. The same hand as the leg working on is used to hold the center of the pod 176 onto the leg so that the V-notches are aligned with the triangle marks. With the other hand, the tab "1" is gently pulled to expose the adhesive on the back of the pod 176. The center of the pod 176 is kept in place as the backing paper is removed. Once the "1" backing paper is removed, the adhesive flap is rolled down so that it sticks to the skin smoothly and without getting wrinkled. The V-notches should still be aligned with the triangle marks. The adhesive is gently pressed onto the skin, making sure it has fully adhered to the skin. Next, the "2" tab is removed from the rest of the backing paper. The rest of the adhesive is rolled onto the skin. The entire adhesive can be smoothed to make sure it has fully adhered to the skin.

Figure 32:
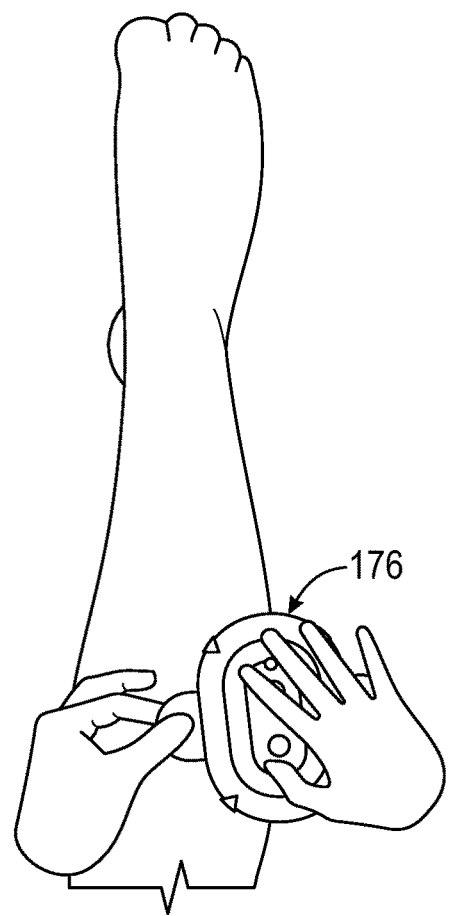

In FIG. 32, another pod 176 is oriented on the lower leg so that the "1" tab is pointing toward the center of the body and the "2" tab is pointing away from the body. Next, the V-notches in the pod are aligned with the triangle marks drawn on the lower leg. Using the same hand as the leg being worked on, the center of the pod 176 is held onto the leg so that the V-notches are aligned with the triangle marks. With the other hand, the "1" tab is removed to expose the adhesive on the back of the pod 176. The center of the pod 176 should be held in place as the backing paper is removed. Once the "1" tab backing paper is removed, the adhesive flap is rolled down so that it sticks to the skin smoothly and without getting wrinkled. The V-notches should still be aligned with the triangle marks. Gently press the adhesive onto the skin, making sure it has fully adhered to the skin. The "2" tab is gently removed to roll the rest of the adhesive onto the skin. Smooth down the entire adhesive to make sure it has fully adhered to the skin.

Figure 33:
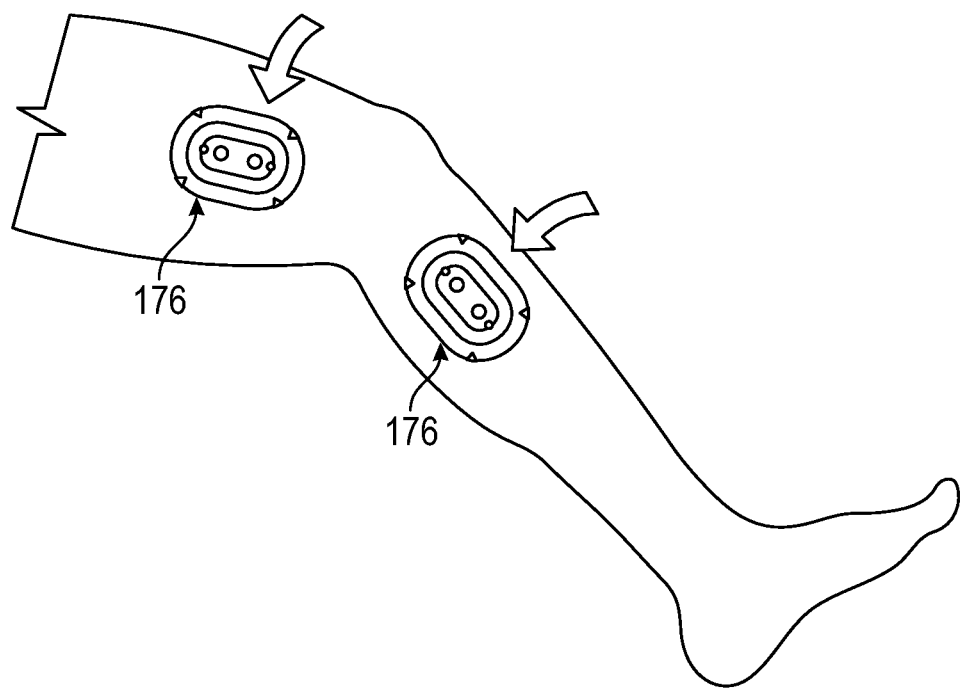
Figure 34:
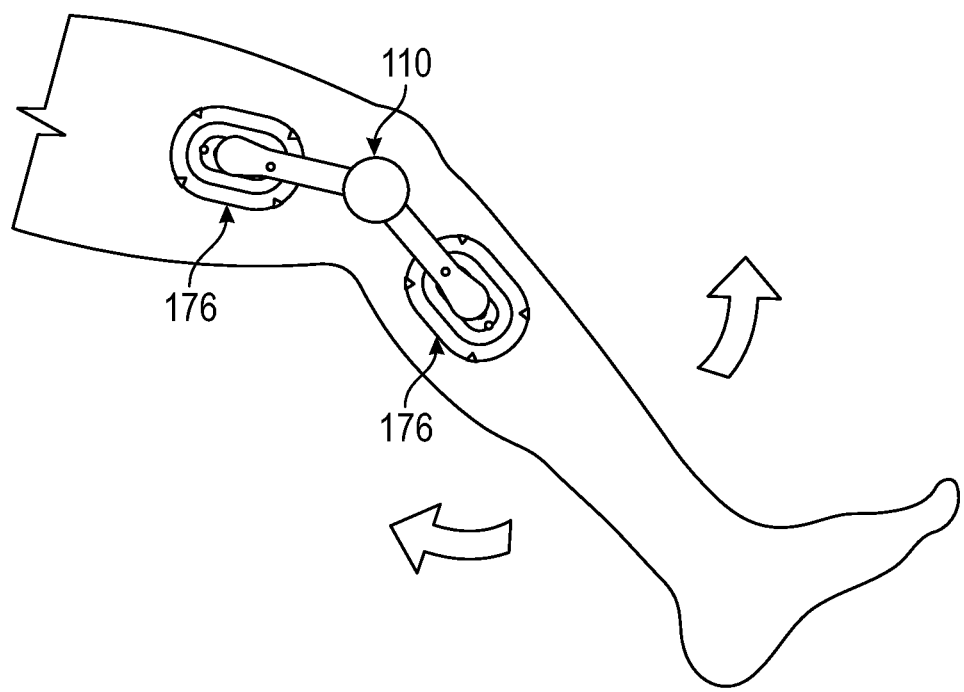

The fingertips can be used to flatten the edges of the adhesive fully against the skin (FIG. 33). Rub gently to increase adhesion for both pods 176. The pods 176 are now changed and the goniometer 110 is ready to attach to the user. Hold the goniometer 110 close to the magnets on the pods 176 and let them snap into place via the magnets. Positioning of the pods 176 can be checked by attaching the goniometer 110 and flexing the leg (FIG. 34). If the goniometer 110 pops off of one or both of the pods 176, the detached pod 176 has been re-applied too far from the correct position. Check to see if any V-notches are not well aligned with the triangle marks on the skin. If this is the case, remove that pod 176 and reapply a new pod 176, making sure it is aligned more closely to the triangle marks on the skin.

Pod Function

A pair of truncated pull tab pod assemblies, one adhered to the upper leg, and one to the lower leg, act as anchors to the ends of the goniometer, which measures the angle of the knee over the course of the patient's sessions. Although the goniometer is removed between sessions, the pair of pods are to be left in place for about a week. Once a week, the patient or caregiver replaces the first set of pod assemblies with new pod assemblies. Repeat weekly. Location targets marked on the legs can be "refreshed" by the patient to provide for repeatable placement locations for each new pair of pod assemblies. The "semi-continuous" measurement anchor points provided by the pods allow for a reliable assessment of range of motion over the duration of the therapy.

Pod Description

The pod assembly can include three basic layers. The bottom layer can be highly compliant, hypoallergenic, breathable, and adheres to the skin. The middle layer can be a thin foam that is moderately compliant. The top layer can be a rigid plastic molded part that has locating features and a pair of magnets and is adhered to the middle layer with an adhesive.

Four location notches in the bottom layer can provide for reliable marking of initial pod locations such that subsequent pods can be placed accurately in the same location and orientation. The middle layer can act as a transitional material between the larger, compliant layer and the smaller pod with snaps. Features in the rigid pod can include the top layer as location features to assemble to the goniometer and to the pod template. The magnets, mating with similar magnets in the goniometer, provide the retention force to allow use of the goniometer during a session. Before assembly to the body, the pod comes from the package with two release papers with large pull tabs that cover the adhesive of the bottom layer.

Pod Design Aspects

The pods can be consistent anchor points for the goniometer. When the goniometer is not in place during a session, either the pods can act as attachment points for the goniometer or a pedometer. For the goniometer to provide relevant and reliable range of motion information for clinical use, the pods can be initially located accurately with respect to physiological landmarks and reliably replaced. The pod assembly allows for accurate initial placement and reliable replacement. A combination of novel features and functions in the pod assembly and the alignment assembly allow for these features. Within the pod assembly, the V-notches in allow for accurate replacement of subsequent pods. The asymmetric release paper adhesive backing and large numbered pull tabs allow for the easy location and highly reliable placement and adhesion to the skin. Once the skin is marked with the four targets triangles, the patient can easily locate and orient a new pod by aligning the V-notches to the marked triangles. This "peel-in-place" feature allows for targeting and adhering to be decoupled. Once the first section of the adhesive is revealed and adhered to the skin it acts as an anchor for the following steps. The patient or caregiver can pull the second pull tab and reveal the rest of the adhesive, and can simply smooth the rest of the pod onto the skin with little concern it will be out of place.

Alignment Assembly Function

The alignment assembly allows physiological landmarks of the patient to be used for accurate pods placements for use with the goniometer. The skin over the lateral epicondyle is located and a circular sticker is placed on the patient's skin or clothing over both the greater trochanter and lateral malleolus. A knee pivot anchor of the alignment assembly can be accurately placed over the lateral epicondyle. The pod is placed with the alignment assembly such that it "points" to either the greater trochanter or lateral malleolus target sticker. Once aligned, the assembly is stabilized and affixed. The process is repeated for other pods as described herein.

Alignment Assembly Description

The alignment arm can be a long chipboard part that has a hole to accept the knee pivot anchor, "pointing" features at the far end to help align with the physiological landmarks, and a hole in the mid-section that aligns to and snaps to features on pods. The distance between these two holes in the template assists in final placement of the pods, and corresponds to hard dimensions in the goniometer. The knee pivot anchor can be a plastic part with a pad of adhesive that snaps into a hole in the end of the template and allows for rotation such that it can be used for both segments of the leg. The center of the anchor can be hollow so that a mark can be placed over the lateral epicondyle. The "skin-side" of the anchor is designed to be flexible, such that the adhesive pad assembled to it can conform to the side of the knee and provide a good adhesion point for use. This part can be removed.

These designs provide accuracy, repeatability, and ease of use for both the patient and the caregiver. The "peel-in-place" release paper design can be superior to the conventional "peel then place" method for the pods. The "mark after placement" method for initial alignment rather than conventional "mark (with a template) then place" method also is an advantage. The release paper can be asymmetric to allow for holding during the first release paper pull. The release paper can use pull tabs to number the release paper in the order of release. In addition to being an ergonomic aid (a "third hand") for stabilizing the assembly to the leg, the locked pivot point, used for both pod placements insures that the pod-to-pod distance will be well controlled, and within the tolerances of use with the corresponding and highly repeatable goniometer geometry.

Other embodiments can include one or more of the following items or components.

900

A system for measuring an angle of a joint of a user, comprising:
a center hub, the center hub having a first hub and a second hub;
a first arm configured for attachment to a first limb portion of the user at a first outer end and to the first hub at a first inner end;
a second arm configured for attachment to a second limb portion of the user at a second outer end and to the second hub at a second inner end, wherein the first hub is pivotally coupled to the second hub;
a magnet coupled to the second hub; and
a sensor disposed in the center hub and configured to detect a rotation of the magnet.

The system further comprising a printed circuit board (PCB) removably disposed in the center hub, the PCB having an inward notch; and an outward notch coupled to the first hub, wherein the outward notch is configured to couple with the inward notch to align the sensor and the magnet.

The system further comprising a cover detachably coupled to the first hub, wherein the cover is configured to inhibit movement of the PCB within the center hub.

The system wherein the sensor is a Hall Effect sensor coupled to the PCB.

The system wherein the sensor is configured to measure the rotation of the magnet up to a precision of about +/−0.01 degree.

The system further comprising a retaining ring configured to couple the magnet to the second hub.

The system wherein the magnet is configured with north and south polarity within the center hub.

The system further comprising a circuit configured to generate an electrical signal based on the rotation of the magnet and to transmit the electrical signal in real time.

The system further comprising a user interface configured to receive the electrical signal and display data obtained from the electrical signal.

The system wherein the data includes the angle of the joint of the user.

The system wherein the first hub and the second hub are configured to rotate 360 degrees about an axis.

A system for measuring an angle of a joint of a user, comprising:
a center hub, the center hub having a first hub and a second hub;
a first arm configured for attachment to a first limb portion of the user at a first outer end and to the first hub at a first inner end;
a second arm configured for attachment to a second limb portion of the user at a second outer end and to the second hub at a second inner end, wherein the first hub is pivotally coupled to the second hub and configured to rotate 360 degrees about an axis;
a magnet coupled to the second hub;
a printed circuit board (PCB) removably disposed in the center hub; and
a sensor coupled to the PCB and configured to detect a rotation of the magnet.

The system further comprising a battery housing coupled to the PCB; and a battery detachably coupled to the battery housing.

The system further comprising a transmitter coupled to the PCB and configured to transmit an electrical signal based on the rotation of the magnet.

The system further comprising a user interface configured to receive the electrical signal and display data obtained from the electrical signal, wherein the data has the angle of the joint of the user.

The system wherein the first and second arms are adhesively attached to respective ones of the first and second limb portions of the user.

A system for measuring an angle of a joint of a user, comprising:
- a center hub, the center hub having a first hub and a second hub, wherein the first hub has an outward notch;
- a first and second coupling apparatus configured to be adhesively attached to first and second limb portions proximal to the joint of the user;
- a first arm configured for attachment to a first coupling apparatus at a first outer end and to the first hub at a first inner end;
- a second arm configured for attachment to a second coupling apparatus at a second outer end and to the second hub at a second inner end, wherein the first hub is pivotally coupled to the second hub;
- a magnet coupled to the second hub;
- a printed circuit board (PCB) having an inward notch and removably disposed in the center hub;
- a sensor coupled to the PCB and configured to detect a rotation of the magnet, wherein the outward notch is configured to fit within the inward notch to align the sensor and the magnet; and
- a transmitter coupled to the PCB and configured to transmit an electrical signal based on the rotation of the magnet, wherein the electrical signal has data of the angle of the joint of the user.

The system further comprising a cover coupled to the center hub, wherein the cover has a snap mechanism configured to attach and detach the cover.

The system wherein the first and second arms have sections configured to rotate the first and second arms about +/−ten degrees.

The system wherein the first and second arms have sections configured to twist the first and second arms about +/−eighteen degrees.

1000

An apparatus for coupling a device to a user, the apparatus comprising:
- a first layer having a top and a bottom, wherein the bottom comprises an adhesive material configured to couple the device to the user;
- a second layer concentric with the first layer and coupled to the top of the first layer, and the second layer is smaller in size than the first layer and has an upper surface area;
- a pod concentric with the second layer and sized to be received by and detachably coupled to the upper surface area, and the pod is configured to detachably couple the pod to the device.

The apparatus wherein, to prevent the apparatus from uncoupling from the user, the second layer comprises a material configured to dampen forces acting between the device and the apparatus and caused by relative movement between the device and the apparatus.

The apparatus wherein the adhesive material is a medical grade adhesive.

The apparatus wherein the upper surface area comprises one of hooks and loops, wherein the pod has an underside comprised of one of hooks and loops, and wherein the upper surface and the underside are detachably coupled by the hooks and loops.

The apparatus wherein the first layer defines a notch for assisting in aligning the apparatus relative to a predetermined location on the user.

The apparatus wherein the notch is V-shaped.

The apparatus wherein the first layer defines a pair of alignment holes.

The apparatus wherein, to facilitate alignment of the apparatus relative to a predetermined location on the user, the upper surface of the second layer comprises an adhesive material to enable detachable coupling between the upper surface and the pod.

The apparatus wherein, when the device couples to the apparatus, the pod defines a recess for positioning and aligning the device relative to the apparatus.

The apparatus wherein the pod comprises a magnet positioned adjacent to the recess to detachably couple the pod to the apparatus.

An apparatus for coupling a device to a user, the apparatus comprising:
- a first layer with a first periphery, and the first layer has a top and a bottom, wherein the bottom comprises an adhesive material configured to couple the apparatus to the user, and the first layer defines a plurality of notches spaced apart from one another and disposed about the first periphery of the first layer, and the first layer defines a pair of alignment holes, and the notches and the alignment holes align the apparatus relative to a predetermined location on the user;
- a second layer smaller in size than, and concentric with, the first layer, and the second layer has a lower surface that couples to the first layer and an upper surface, wherein the upper surface presents an area that comprises an adhesive material;
- a pod concentric with the second layer and sized to be received by and detachably coupled to the area of the upper surface area, and the pod has a magnet to allow the pod to be detachably coupled to the device, and the pod defines a recess for positioning and aligning the device relative to the apparatus when the device couples to the pod.

The apparatus wherein, to prevent the apparatus from uncoupling from the user, the second layer comprises a material configured to dampen forces acting between and caused by relative movement between the device and the apparatus.

An apparatus for measuring flexion and extension of a joint of a user, said apparatus comprising:
- a first attachment and a second attachment, each comprising:
  - a first layer with a top and a bottom, wherein the bottom comprises an adhesive material for coupling, on opposite sides of the joint, the attachments to the user;
  - a second layer concentric with the first layer, and the second layer has a lower surface that couples to the first layer and an upper surface; and
  - a pod concentric with the second layer and detachably coupled to the upper surface; and
- a goniometer for measuring flexion and extension of the joint of the user, and the goniometer is detachably coupled to, and spans between, the pods of the attachments.

The apparatus wherein, to prevent the attachments from uncoupling from the user, the second layer comprises a material configured to dampen forces acting between the goniometer and the attachments and caused by relative movement between the goniometer and the attachments.

The apparatus wherein the goniometer has a pair of arms rotatably coupled to and about a center hub, and each arm has a boss for aligning and coupling each arm to a respective pod.

The apparatus wherein each pod defines a recess for receiving and detachably coupling to one of the bosses of the goniometer, and for positioning the goniometer relative to each attachment.

The apparatus wherein, to prevent the goniometer from uncoupling from the attachments, the bosses are sized to be movable within the recesses to allow movement of the bosses in the recesses.

The apparatus wherein, to detachably couple the goniometer to the attachments, magnets are disposed adjacent to each boss and each recess.

The apparatus wherein wings extend outwardly from the sides of each arm of the goniometer configured to enable a user to move the arms of the goniometer perpendicularly relative to the attachments, and to uncouple the goniometer from the attachments.

The apparatus wherein the edges of the pod are tapered, such configuration enabling a user to further move the arms of the goniometer perpendicularly relative to the attachments, and to uncouple the goniometer from the attachments.

1010

An apparatus for coupling a device to a user, the apparatus comprising:
 a first layer having a top and a bottom, wherein the bottom comprises an adhesive material configured to couple the device to the user;
 a second layer concentric with the first layer and coupled to the top of the first layer, and the second layer is smaller in size than the first layer and has an upper surface area;
 a pod concentric with the second layer and sized to be received by and detachably coupled to the upper surface area, and the pod is configured to detachably couple the pod to the device; and
 a pedometer configured to count steps of the user and configured to be removably attached to the apparatus.

The apparatus wherein, to prevent the apparatus from uncoupling from the user, the second layer comprises a material configured to dampen forces acting between the device and the apparatus and caused by relative movement between the device and the apparatus.

The apparatus wherein the adhesive material is a medical grade adhesive.

The apparatus wherein the upper surface area comprises one of hooks and loops, wherein the pod has an underside comprised of one of hooks and loops, and wherein the upper surface and the underside are detachably coupled by the hooks and loops.

The apparatus wherein the first layer defines a notch for assisting in aligning the apparatus relative to a predetermined location on the user.

The apparatus wherein the notch is V-shaped.

The apparatus wherein the first layer defines a pair of alignment holes.

The apparatus wherein, to facilitate alignment of the apparatus relative to a predetermined location on the user, the upper surface of the second layer comprises an adhesive material to enable detachable coupling between the upper surface and the pod.

The apparatus wherein, when the device couples to the apparatus, the pod defines a recess for positioning and aligning the device relative to the apparatus.

The apparatus wherein the pod comprises a magnet positioned adjacent to the recess to detachably couple the pod to the apparatus.

An apparatus for coupling a device to a user, the apparatus comprising:
 a first layer with a first periphery, and the first layer has a top and a bottom, wherein the bottom comprises an adhesive material configured to couple the apparatus to the user, and the first layer defines a plurality of notches spaced apart from one another and disposed about the first periphery of the first layer, and the first layer defines a pair of alignment holes, and the notches and the alignment holes align the apparatus relative to a predetermined location on the user;
 a second layer smaller in size than, and concentric with, the first layer, and the second layer has a lower surface that couples to the first layer and an upper surface, wherein the upper surface presents an area that comprises an adhesive material;
 a pod concentric with the second layer and sized to be received by and detachably coupled to the area of the upper surface area, and the pod has a magnet to allow the pod to be detachably coupled to the device, and the pod defines a recess for positioning and aligning the device relative to the apparatus when the device couples to the pod; and
 a pedometer configured to count steps of the user and configured to be removably attached to the apparatus.

The apparatus wherein, to prevent the apparatus from uncoupling from the user, the second layer comprises a material configured to dampen forces acting between and caused by relative movement between the device and the apparatus.

An apparatus for measuring flexion and extension of a joint of a user, said apparatus comprising:
 a first attachment and a second attachment, each comprising:
 a first layer with a top and a bottom, wherein the bottom comprises an adhesive material for coupling, on opposite sides of the joint, the attachments to the user;
 a second layer concentric with the first layer, and the second layer has a lower surface that couples to the first layer and an upper surface; and
 a pod concentric with the second layer and detachably coupled to the upper surface; and
 a goniometer for measuring flexion and extension of the joint of the user, and the goniometer is detachably coupled to, and spans between, the pods of the attachments; and
 a pedometer configured to count steps of the user and configured to be removably attached to the apparatus.

The apparatus wherein, to prevent the attachments from uncoupling from the user, the second layer comprises a material configured to dampen forces acting between the goniometer and the attachments and caused by relative movement between the goniometer and the attachments.

The apparatus wherein the goniometer has a pair of arms rotatably coupled to and about a center hub, and each arm has a boss for aligning and coupling each arm to a respective pod.

The apparatus wherein each pod defines a recess for receiving and detachably coupling to one of the bosses of the goniometer, and for positioning the goniometer relative to each attachment.

The apparatus wherein, to prevent the goniometer from uncoupling from the attachments, the bosses are sized to be movable within the recesses to allow movement of the bosses in the recesses.

The apparatus wherein, to detachably couple the goniometer to the attachments, magnets are disposed adjacent to each boss and each recess.

The apparatus wherein wings extend outwardly from the sides of each arm of the goniometer configured to enable a user to move the arms of the goniometer perpendicularly relative to the attachments, and to uncouple the goniometer from the attachments.

The apparatus wherein the edges of the pod are tapered, such configuration enabling a user to further move the arms of the goniometer perpendicularly relative to the attachments, and to uncouple the goniometer from the attachments.

1500

An apparatus for measuring flexion and extension at a joint of a user, the apparatus comprising:
  a center hub having a first hub, and a second hub coaxially aligned with and rotatably coupled to the first hub;
  a first arm coupled to and rotatable with the first hub; and
  a second arm coupled to and rotatable with the second hub wherein, to maintain a position of the center hub relative to the joint of the user, the first and second arms pivotably and rotatably couple to a respective first and second hub such that rotation, flexion, and extension of the first and second arms are allowed.

The apparatus of claim 1, wherein each of the first and second arms comprise an inner link for pivotably coupling the first and second arms to the first and second hubs, and the inner links are configured to allow the first and second arms to flex and extend relative to the center hub.

The apparatus wherein each of the first and second arms comprise an outer link coupled to the inner link, and the outer links are configured to rotate the first and second arms relative to the center hub.

The apparatus further comprising a screw configured to couple one of the inner and one of the outer links, wherein the screw is aligned parallel to a length of a respective one of the first and second arms, and wherein, to allow the rotation of the first and second arms relative to the center hub, the screw provides for rotation of the inner and outer links.

The apparatus wherein each of the first and second arms comprises an outer end coupled to the outer link, and the outer end is configured to flex and extend relative to the center hub such that further flexion and extension of the first and second arms relative to the center hub are enabled.

The apparatus further comprising link arms extending outwardly from each of the first and second hubs, wherein the link arms couple to respective ones of the first and second arms.

The apparatus further comprising pins configured to couple between a respective outer link and a respective outer end, and between a respective inner link and a respective link arm, and wherein the pins are aligned perpendicular to a length of a respective arm, and wherein the pins provide for the flexion and extension of the first and second arms relative to the center hub.

The apparatus wherein the arms include a magnet and a boss.

An apparatus for measuring flexion and extension at a joint of a user, the apparatus comprising:
  a center hub that has an upper hub, and a lower hub coaxially aligned with and rotatably coupled to the upper hub;
  an arm coupled to, and rotatable with, each of the upper and lower hubs, and the arms pivotably and rotatably couple to the hubs to allow rotation, flexion, and extension of the arms, and to restrict movement of the center hub relative to the joint of the user.

The apparatus further comprising link arms that extend outwardly from each of the upper and lower hubs, and the arms couple to a respective hub at a respective link arm.

The apparatus wherein pins couple each of the link arms and each of the arms, and the pins are aligned perpendicular to the length of a respective arm and configured to allow flexion and extension of the arms, and a screw couples between each of the link arms and each of the arms, and each screw is aligned parallel with the length of a respective arm configured to allow rotation of each arm about each screw.

The apparatus wherein the arms include a magnet and a boss for aligning and coupling the arms to attachments.

An apparatus for measuring flexion and extension at a joint of a user, the apparatus comprising:
  a center hub comprising:
    an upper hub and a first link arm that extends outwardly from the upper hub;
    a lower hub coaxially aligned with and rotatably coupled to the upper hub, and a second link arm extends outwardly from the lower hub;
    an arm pivotably coupled to each of the first and second link arms, and each arm comprises:
      an inner link for pivotably coupling the arm to a respective first and second link arm and for allowing the arm to flex and extend relative to the center hub;
      an outer link rotatably coupled to the inner link to allow the arm to rotate relative to the center hub;
      an outer end pivotably coupled to the outer link to allow the outer end of the arm to flex and extend relative to the outer link and the center hub.

The apparatus wherein the link arms are integrally formed with the hubs.

The apparatus wherein the link arms are coupled to the respective hubs, and the link arms are configured to allow flexion and extension of the arms relative to the center hub.

The apparatus wherein the link arms couple to the respective hubs and are configured to allow rotation of the arms relative to the center hub.

The apparatus wherein a pin couples the inner link and the link arm, and the pin is aligned perpendicular to the length of the arm, and the pin provides for the pivotable coupling between the inner links and link arm.

The apparatus wherein a pin couples the outer link and the outer end, and the pin is aligned perpendicular to the length of the arm, and the pin provides for the pivotable coupling between the outer link and the outer end.

The apparatus wherein a screw couples the inner and outer link, and the screw is aligned parallel with the length of the arm, and the screw provides for the rotatable coupling between the inner link and outer link.

The apparatus wherein the arms include a magnet and a boss.

1700

An apparatus for assisting a person in aligning, relative to a center of a joint of a user, a wearable device on opposing limb portions of the joint of the user, the wearable device has attachments, each attachment defines alignment holes spaced from each other, and the alignment holes have a size, the apparatus comprising:
  a first segment;
  a second segment coupled to the first segment at a pivot point, and when positioned adjacent the center of the joint, the pivot point aligns the apparatus relative to the center of the joint;

the first and second segments each defining voids, the voids are spaced on each of the first and second segments equidistant from the pivot point, and the spacing between, and size of, the voids is commensurate with the spacing between, and size of, the alignment holes of the respective attachments; and whereby the person pivots the segments to centrally align the segments relative to the respective opposing limb portions of the user, and the person marks locations on the respective opposing limb portions through the voids, wherein the alignment holes of the attachments are aligned with respective marks to align the attachments and to couple the wearable device to the user.

The apparatus wherein the first and second segments each have center axes, the center axes intersect at the pivot point, and prior to marking locations on the respective opposing limb portions, the person pivots each segment to centrally align the center axes with the respective centers of the opposing limb portions.

The apparatus wherein the second segment pivotably couples to the first segment at the pivot point.

The apparatus wherein the second segment couples to the first coupling end at a pivot point by overlaying with the first segment.

The apparatus wherein the pivot point is spaced adjacent to and equidistant from first and second coupling ends of the respective first and second segments.

The apparatus wherein the alignment holes of the attachments are aligned coaxially with respective marks to align the attachments, and enable the wearable device to be mounted on the user.

A method for assisting a person in aligning a wearable device relative to a center of a joint of a user, on opposing limb portions of the joint of the user, the wearable device has attachments, each attachment defines alignment holes spaced from each other, and each alignment hole has a size, the method comprising:
  providing an apparatus having a first segment and a second segment pivotably coupled to the first segment at a pivot point;
  providing voids defined in each of the first and second segments, the voids are spaced an equidistant from the pivot point on each of the first and second segments, and the spacing between, and size of, the voids is commensurate with the spacing between, and size of, the alignment holes of the respective attachments;
  locating the center of the joint;
  aligning the pivot point of the apparatus with the center of the joint;
  pivoting each segment to centrally align the segments relative to respective opposing limb portions;
  marking locations on the respective opposing limb portions through the voids;
  positioning the alignment holes of the attachments with respective marks to align the attachments and the wearable device on the user; and
  coupling the attachments and the wearable device to the user.

The method further comprising:
  providing center axes of the first and second segments, and the center axes intersect at the pivot point;
  pivoting each segment to centrally align the center axes with the center of the respective opposing limb portion.

The method further comprising:
  providing pegs; and
  coaxially aligning the pegs with the markings to facilitate alignment of the alignment holes of the attachments with each mark.

The method wherein the step of locating the center of the joint is further defined as locating the lateral epicondyle of a knee joint.

An apparatus for assisting a person in aligning a wearable device relative to a center of a joint of a user, on opposing limb portions of the joint of the user, the wearable device has attachments, each attachment defines alignment holes spaced from each other, and the alignment holes have a size, the apparatus comprising:
  an imaging device for locating a position of the joint of the user and the opposing limb portions;
  a laser configured to provide a beam of light;
  a processor in communication with the imaging device and the laser; and
  the processor is configured to receive and process data from the imaging device representative of the position of the joint of the user and the opposing limb portions, the processor communicates with the lasers to position the laser such that the light beam forms spots of light on the user at the center of the joint and on the opposing limb portions of the user commensurate with the spacing between, and size of, the alignment holes of the respective attachments, and wherein the alignment holes of the attachments are aligned with respective alignment holes of the attachments to couple the wearable device on the user.

A method for assisting a person in aligning a wearable device relative to a center of a joint of a user, on opposing limb portions of the joint of the user, the wearable device has attachments, each attachment defines alignment holes spaced from each other, and each alignment hole has a size, the method comprising:
  providing an imaging device;
  providing a laser configured to provide a beam of light;
  providing a processor configured to communicate with the imaging device and the laser;
  locating with the imaging device positions of the joint and the opposing limb portions;
  communicating data from the imaging device to the processor, the data being representative of the positions of the joint and the opposing limb portions;
  processing the data with the processor;
  calculating with the processor positions of the laser to provide the laser beam to form spots of light on the user at the center of the joint and the opposing limb portions, and the foregoing is commensurate with the spacing between, and size of, the alignment holes of the respective attachments;
  communicating instructions to the laser;
  moving the laser to the positions; and
  aligning the alignment holes of the attachments with the respective spots of light to align the attachments and to couple the wearable device to the user.

The method further comprising the step of marking on the opposing limb portions the location of the laser beam, and aligning the alignment holes of the attachments coaxial with respective marks to align the attachments and to couple the wearable device to the user.

An apparatus for assisting a person in aligning a wearable device relative to a center of a joint of a user and on opposing limb portions of the joint of the user, the apparatus comprising:
  diodes coupled to the wearable device, the joint, and the opposing limb portions;

an imaging device for locating positions of the diodes;
a personal communication device configured to communicate with a person;
a processor in communication with the imaging device and the personal communication device; and
the processor is configured to receive and process data from the imaging device representative of the positions of the diodes, and the processor communicates with the personal communication device to provide instructions representative of action to be taken by the person to align the wearable device relative to the center of joint of the user.

The apparatus wherein the personal communication device is a display.

The apparatus wherein the personal communication device is a speaker.

A method for assisting a person in aligning a wearable device on opposing limb portions of a joint of a user relative to a center of the joint of the user, the method comprising:
providing a diode coupled to the wearable device, the joint, and the opposing limb portions of the user;
providing an imaging device for locating a position of the diodes;
providing a personal communication device configured to communicate with a person;
providing a processor configured to communicate with the imaging device and the personal communication device;
locating with the imaging device the position of the diodes;
communicating, from the imaging device to the processor, data representative of the position of the diodes;
processing of the data by the processor;
calculating by the processor a position of the wearable device relative to the joint and the opposing limb portions;
calculating by the processors a position of the wearable device, and instructions for the person to align the wearable device relative to the center of the joint of the patient;
communicating by the processors to the personal communication device the instructions to be provided to the person for aligning the wearable device relative to the center of the joint of the user; and
communicating to the person with the personal communication device.

The method wherein the step of communicating to the person with the personal communication device further comprises providing audio instruction through a speaker to the personal communication device.

The method wherein the step of communication to the person with the communication device further comprises providing visual instruction through a display to the personal communication device.

An apparatus for assisting a person in aligning, relative to a center of a joint of a user, a wearable device on opposing limb portions of the joint of the user, the wearable device has attachments, each attachment defines alignment holes spaced from each other, and the alignment holes have a size, the apparatus comprising:
a first segment;
a second segment coupled to the first segment at a pivot point, and when positioned adjacent the center of the joint, the pivot point aligns the apparatus relative to the center of the joint;
the first and second segments each defining voids, the voids are spaced on each of the first and second segments equidistant from the pivot point, and the spacing between, and size of, the voids is commensurate with the spacing between, and size of, the alignment holes of the respective attachments; and
whereby the person pivots the segments to centrally align the segments relative to the respective opposing limb portions of the user, and the person marks locations on the respective opposing limb portions through the voids, wherein the alignment holes of the attachments are aligned with respective marks to align the attachments and to couple the wearable device to the user.

The apparatus wherein the first and second segments each have center axes, the center axes intersect at the pivot point, and prior to marking locations on the respective opposing limb portions, the person pivots each segment to centrally align the center axes with the respective centers of the opposing limb portions.

The apparatus wherein the second segment pivotably couples to the first segment at the pivot point.

The apparatus wherein the second segment couples to the first coupling end at a pivot point by overlaying with the first segment.

The apparatus wherein the pivot point is spaced adjacent to and equidistant from first and second coupling ends of the respective first and second segments.

The apparatus wherein the alignment holes of the attachments are aligned coaxially with respective marks to align the attachments, and enable the wearable device to be mounted on the user.

A method for assisting a person in aligning a wearable device relative to a center of a joint of a user, on opposing limb portions of the joint of the user, the wearable device has attachments, each attachment defines alignment holes spaced from each other, and each alignment hole has a size, the method comprising:
providing an apparatus having a first segment and a second segment pivotably coupled to the first segment at a pivot point;
providing voids defined in each of the first and second segments, the voids are spaced an equidistant from the pivot point on each of the first and second segments, and the spacing between, and size of, the voids is commensurate with the spacing between, and size of, the alignment holes of the respective attachments;
locating the center of the joint;
aligning the pivot point of the apparatus with the center of the joint;
pivoting each segment to centrally align the segments relative to respective opposing limb portions;
marking locations on the respective opposing limb portions through the voids;
positioning the alignment holes of the attachments with respective marks to align the attachments and the wearable device on the user; and
coupling the attachments and the wearable device to the user.

The method further comprising:
providing center axes of the first and second segments, and the center axes intersect at the pivot point;
pivoting each segment to centrally align the center axes with the center of the respective opposing limb portion.

The method further comprising:
providing pegs; and
coaxially aligning the pegs with the markings to facilitate alignment of the alignment holes of the attachments with each mark.

The method wherein the step of locating the center of the joint is further defined as locating the lateral epicondyle of a knee joint.

An apparatus for assisting a person in aligning a wearable device relative to a center of a joint of a user, on opposing limb portions of the joint of the user, the wearable device has attachments, each attachment defines alignment holes spaced from each other, and the alignment holes have a size, the apparatus comprising:
- an imaging device for locating a position of the joint of the user and the opposing limb portions;
- a laser configured to provide a beam of light;
- a processor in communication with the imaging device and the laser; and
- the processor is configured to receive and process data from the imaging device representative of the position of the joint of the user and the opposing limb portions, the processor communicates with the lasers to position the laser such that the light beam forms spots of light on the user at the center of the joint and on the opposing limb portions of the user commensurate with the spacing between, and size of, the alignment holes of the respective attachments, and wherein the alignment holes of the attachments are aligned with respective alignment holes of the attachments to couple the wearable device on the user.

A method for assisting a person in aligning a wearable device relative to a center of a joint of a user, on opposing limb portions of the joint of the user, the wearable device has attachments, each attachment defines alignment holes spaced from each other, and each alignment hole has a size, the method comprising:
- providing an imaging device;
- providing a laser configured to provide a beam of light;
- providing a processor configured to communicate with the imaging device and the laser;
- locating with the imaging device positions of the joint and the opposing limb portions;
- communicating data from the imaging device to the processor, the data being representative of the positions of the joint and the opposing limb portions;
- processing the data with the processor;
- calculating with the processor positions of the laser to provide the laser beam to form spots of light on the user at the center of the joint and the opposing limb portions, and the foregoing is commensurate with the spacing between, and size of, the alignment holes of the respective attachments;
- communicating instructions to the laser;
- moving the laser to the positions; and
- aligning the alignment holes of the attachments with the respective spots of light to align the attachments and to couple the wearable device to the user.

The method further comprising the step of marking on the opposing limb portions the location of the laser beam, and aligning the alignment holes of the attachments coaxial with respective marks to align the attachments and to couple the wearable device to the user.

An apparatus for assisting a person in aligning a wearable device relative to a center of a joint of a user and on opposing limb portions of the joint of the user, the apparatus comprising:
- diodes coupled to the wearable device, the joint, and the opposing limb portions;
- an imaging device for locating positions of the diodes;
- a personal communication device configured to communicate with a person;
- a processor in communication with the imaging device and the personal communication device; and
- the processor is configured to receive and process data from the imaging device representative of the positions of the diodes, and the processor communicates with the personal communication device to provide instructions representative of action to be taken by the person to align the wearable device relative to the center of joint of the user.

The apparatus wherein the personal communication device is a display.

The apparatus wherein the personal communication device is a speaker.

A method for assisting a person in aligning a wearable device on opposing limb portions of a joint of a user relative to a center of the joint of the user, the method comprising:
- providing a diode coupled to the wearable device, the joint, and the opposing limb portions of the user;
- providing an imaging device for locating a position of the diodes;
- providing a personal communication device configured to communicate with a person;
- providing a processor configured to communicate with the imaging device and the personal communication device;
- locating with the imaging device the position of the diodes;
- communicating, from the imaging device to the processor, data representative of the position of the diodes;
- processing of the data by the processor;
- calculating by the processor a position of the wearable device relative to the joint and the opposing limb portions;
- calculating by the processors a position of the wearable device, and instructions for the person to align the wearable device relative to the center of the joint of the patient;
- communicating by the processors to the personal communication device the instructions to be provided to the person for aligning the wearable device relative to the center of the joint of the user; and
- communicating to the person with the personal communication device.

The method wherein the step of communicating to the person with the personal communication device further comprises providing audio instruction through a speaker to the personal communication device.

The method wherein the step of communication to the person with the communication device further comprises providing visual instruction through a display to the personal communication device.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The various aspects, embodiments, implementations or features of the described embodiments may be used separately or in any combination. The embodiments disclosed herein are modular in nature and may be used in conjunction with or coupled to other embodiments.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all of the claims.

Consistent with the above disclosure, the examples of assemblies enumerated in the following clauses are specifically contemplated and are intended as a non-limiting set of examples.

What is claimed:

1. A system for positioning a wearable device for measuring an angle of a joint of a user, the system comprising:
   the wearable device;
   an alignment device separate from the wearable device and including a first segment and a second segment pivotably coupled to the first segment at a pivot point, wherein each of the first segment and the second segment of the alignment device defines first and second voids, and wherein the first voids of the first segment and the second segment are equidistant from the pivot point and the second voids of the first and second segment are equidistant from the pivot point; and
   first and second attachment portions separate from the wearable device and the alignment device and configured to adhesively couple to the user, wherein each of the attachment portions defines at least one alignment hole, wherein each of the attachment portions is configured for securing the wearable device to a corresponding limb portion of the user adjacent to the joint, and wherein the alignment device is configured to facilitate alignment of the first and second attachment portions to the joint,
   wherein the first and second voids of each of the first segment and the second segment have a spacing and a size that is commensurate with the at least one alignment hole in a corresponding attachment portion of the first and second attachment portions to facilitate alignment of the first and second attachment portions to the joint,
   wherein the wearable device includes
      a first hub pivotally coupled to a second hub, a first arm attached to the first hub at a first inner end and defining a first outer end opposite the first inner end, and a second arm attached to the second hub at a second inner end and defining a second outer end opposite the second inner end, and
      wherein each of the first and second attachment portions includes a pod configured to be selectively coupled to a corresponding one of the first outer end of the first arm and the second outer end of the second arm.

2. The system of claim 1, wherein the first and second voids in each of the first segment and the second segment define a straight line with the pivot point.

3. The system of claim 1, wherein the wearable device defines an axis of rotation about which the first hub is pivotally coupled to the second hub, and
   wherein the first and second voids of each of the first segment and the second segment are configured for positioning the first and second attachment portions at specific locations on the corresponding limb portions of the user to cause the axis of rotation to be aligned with a pivot axis of the joint.

4. The system of claim 1, wherein the pods are each selectively coupled to the corresponding one of the first arm and the second arm using magnets.

5. The system of claim 1, wherein at least one of the first arm and the second arm defines a boss, and
   wherein the pods each define a recess configured to receive the boss of a corresponding one of the one of the first arm and the second arm.

* * * * *